United States Patent
Pfeiffer et al.

(10) Patent No.: US 12,125,696 B2
(45) Date of Patent: Oct. 22, 2024

(54) METAL FIXING MATERIAL LEADTHROUGH HAVING LOW SUSCEPTIBILITY TO FAULTS

(71) Applicant: SCHOTT AG, Mainz (DE)

(72) Inventors: Thomas Pfeiffer, Kumhausen (DE); Helmut Hartl, Vienna (AT); Reinhard Ranftl, Pfeffenhausen (DE); Ondrej Rousek, Zamberk (CZ); Susumu Nishiwaki, Kokashi (JP); Robert Hettler, Kumhausen (DE)

(73) Assignee: Schott AG, Mainz (DE)

( * ) Notice: Subject to any disclaimer, the term of this patent is extended or adjusted under 35 U.S.C. 154(b) by 948 days.

(21) Appl. No.: 17/153,518

(22) Filed: Jan. 20, 2021

(65) Prior Publication Data
US 2021/0140745 A1   May 13, 2021

Related U.S. Application Data

(63) Continuation of application No. PCT/EP2019/068960, filed on Jul. 15, 2019.

(30) Foreign Application Priority Data

Jul. 20, 2018 (DE) .................. 10 2018 005 733

(51) Int. Cl.
*H01J 61/36* (2006.01)
*B60R 21/26* (2011.01)
(Continued)

(52) U.S. Cl.
CPC ............ *H01J 61/366* (2013.01); *B60R 21/26* (2013.01); *B60R 22/34* (2013.01); *C03C 27/02* (2013.01);
(Continued)

(58) Field of Classification Search
CPC .. H01J 61/366; H01M 50/186; H01M 50/191; B60R 21/26; B60R 22/34;
(Continued)

(56) References Cited

U.S. PATENT DOCUMENTS 1,813,906 A   7/1931 Caron
3,274,937 A   9/1966 Kyle
(Continued)

FOREIGN PATENT DOCUMENTS

DE   10 2006 004 036 A1   8/2007
DE   10 2006 056 077 A1   5/2008
(Continued)

OTHER PUBLICATIONS

International Search Report dated Dec. 20, 2019 for International Application No. PCT/EP2019/068960 (9 pages).
(Continued)

*Primary Examiner* — Stanley Tso
(74) *Attorney, Agent, or Firm* — Taylor IP, P.C.

(57) ABSTRACT

A metal fixing material leadthrough for igniters of airbags and/or belt tighteners includes at least one metal pin fused into a glass or glass-ceramic fixing material in a through-opening of a main body. The metal is present in a post-heated state, with an interface between the fixing material and the metal pin and an additional interface between the fixing material and an inner surface of the through-opening. The at least one metal pin, at least in its core region, consists of stainless steel, such as a chromium-containing stainless steel, the stainless steel having a thermal expansion coefficient.

43 Claims, 8 Drawing Sheets

(51) Int. Cl.
  *B60R 22/34* (2006.01)
  *C03C 27/02* (2006.01)
  *F42B 3/107* (2006.01)
  *F42B 3/11* (2006.01)
  *H01B 17/30* (2006.01)
  *H01M 50/186* (2021.01)
  *H01M 50/191* (2021.01)
  *F42B 3/198* (2006.01)

(52) U.S. Cl.
  CPC .............. *F42B 3/107* (2013.01); *F42B 3/11* (2013.01); *H01B 17/305* (2013.01); *H01M 50/186* (2021.01); *H01M 50/191* (2021.01); *B60R 2021/26029* (2013.01); *F42B 3/198* (2013.01)

(58) Field of Classification Search
  CPC .......... B60R 2021/26029; C03C 27/02; F42B 3/107; F42B 3/11; F42B 3/198; H01B 17/305
  USPC .................................................. 174/152 GM
  See application file for complete search history.

(56) References Cited

U.S. PATENT DOCUMENTS

| | | | |
|---|---|---|---|
| 5,345,872 A | 9/1994 | Takahashi et al. | |
| 8,176,851 B2 | 5/2012 | Kodama et al. | |
| 2004/0216631 A1 | 11/2004 | Fink et al. | |
| 2006/0222881 A1 | 10/2006 | Fink et al. | |
| 2007/0187934 A1 | 8/2007 | Fink | |
| 2009/0044715 A1 | 2/2009 | Hartl et al. | |
| 2013/0305948 A1 | 11/2013 | Hinkofer et al. | |

FOREIGN PATENT DOCUMENTS

| | | |
|---|---|---|
| DE | 10 2010 045 624 A1 | 3/2012 |
| DE | 20 2010 018 430 U1 | 8/2016 |
| EP | 0 248 977 A1 | 2/1987 |
| EP | 1 455 160 A1 | 9/2004 |
| EP | 1 491 848 A1 | 12/2004 |
| EP | 1 813 906 A1 | 8/2007 |
| EP | 2 270 417 A2 | 1/2011 |
| EP | 2 431 703 A2 | 3/2012 |
| JP | 10-47892 A | 2/1998 |
| WO | 2012/110242 A1 | 8/2012 |
| WO | 2012/110245 A1 | 8/2012 |

OTHER PUBLICATIONS

International Preliminary Report on Patentability dated Jan. 26, 2021 for International Application No. PCT/ EP2019/068960 (18 pgs).

English translation of International Preliminary Report on Patentability dated Jan. 26, 2021 for International Application No. PCT/ EP2019/068960 (13 pgs).

$$M^0 \Rightarrow M^{2+} + e^-$$  $$H_2O + \frac{1}{2}O_2 + 2e^- \Rightarrow 2OH^-$$

METAL FIXING MATERIAL LEADTHROUGH HAVING LOW SUSCEPTIBILITY TO FAULTS

CROSS REFERENCE TO RELATED APPLICATIONS

This is a continuation of PCT application no. PCT/EP2019/068960, entitled "METAL FIXING MATERIAL LEADTHROUGH HAVING LOW SUSCEPTIBILITY TO FAULTS", filed Jul. 15, 2019, which is incorporated herein by reference. PCT application no. PCT/EP2019/068960 claims the priority of German patent application no. 10 2018 005 733.0 entitled "METAL FIXING MATERIAL LEADTHROUGH HAVING LOW SUSCEPTIBILITY TO FAULTS", filed on Jul. 20, 2018, which is incorporated herein by reference.

BACKGROUND OF THE INVENTION

1. Field of the Invention

The present invention relates to a metal fixing material leadthrough, such as for equipment, which can be exposed to high pressures, for example personal protection equipment such as igniters of airbags or belt tensioners, with at least one metal pin, that is fused into a fixing material, such as a glass or glass-ceramic material.

2. Description of the Related Art

Metal fixing material leadthroughs in various versions are already known in the state of the art.

Metal fixing material leadthroughs comprise a vacuum-tight fusion of fixing materials, in particular, glasses, glass-ceramics or plastics with metals. The metals act therein as electrical conductors.

U.S. Pat. Nos. 5,345,872 A or 3,274,937 A are referred to as representative examples. Such leadthroughs are widely used in electronics and electrical engineering. The material used for fusing, in particular, glass, serves as an insulator. Typical metal fixing material leadthroughs are constructed in such a way that metallic inner conductors are inserted into a glass material, whereby the glass material is smelted into an outer metal part, the so-called main body, which is formed from a ring or plate-shaped element.

Preferred applications of such metal fixing material leadthroughs are, for example, ignition devices. Among other things, these are used for airbags or belt tensioners in motor vehicles. In this case, the metal fixing material leadthroughs are part of the ignition device. In addition to the metal fixing material leadthrough, the overall ignition device comprises an ignition bridge, the explosive and a metal cover which tightly encloses the ignition mechanism. Either one, or two, or more than two, metal pins can be passed through the leadthrough. In a particularly preferred embodiment with one metallic pin, the housing is connected to ground, in a preferred two-pole embodiment the ground is connected to one of the pins.

Metal fixing material leadthroughs, in particular, for igniters of airbags or belt tensioners, which are characterized by the fact that the through opening for the metal pins is punched out of the main body, have become known from US 2006/0222881 A1, US 2004/0216631 A, EP 1 455 160 A, US 2007/0187934 A1, as well as U.S. Pat. No. 1,813,906 A. During manufacture of the main body according to US 2007/0187934 A1, the openings are punched through the entire thickness of the main body D from a plate material with a thickness in the range of 1 mm to 5 mm, preferably 1.5 mm to 3.5 mm, particularly preferably of 1.8 mm to 3.0 mm, most particularly preferably of 2.0 mm and 2.6 mm.

The main body is generally also called a header.

In the case of the leadthrough known from WO 2012/110 242 A1, a main body, into which a conductor is glazed, is hermetically sealed in a housing by welding, soldering, press-fitting, crimping in or shrinking in. In WO 2012/110 242 A1, the housing part and/or the main body, preferably the essentially ring-shaped main body, comprise as material a metal, in particular, a light metal, such as titanium, a titanium alloy, magnesium, a magnesium alloy, an aluminum alloy, aluminum, AlSiC, but also steel, high-grade steel or stainless steel.

The metal pin in the fixing material is inserted, in particular, glazed, through the entire thickness D of the main body, the aforementioned region being in the through-opening punched into the main body. Glazing is achieved by first smelting the metal pin into the fixing material, for example, a glass plug. The metal pin with the glass material is then inserted into the through-opening and the metal pin, glass material and main body are heated in such a way that after cooling the metal, the metal of the main body preferably shrinks onto the fixing material, for example, the glass plug.

Since the coefficient of expansion of the main body is greater than that of the fixing material, after cooling, there is compression glass-to-metal sealing, in particular, hermetic compression glass-to-metal sealing.

Hermetic sealing in this application means that the helium leakage rate is less than $1 \times 10^{-8}$ mbar 1/sec.

In order to produce a long-term compression glass-to-metal sealing which is permanently tight even after cooling and subsequent thermal cycles in the operating state, it is assumed in the state of the art and, in particular, in the case of igniters of personal protection equipment such as airbags and/or belt tensioners, that the coefficients of thermal expansion of the materials involved must exhibit certain ratios to one another. Since, in the case of compression glass-to-metal sealing, the main body is intended to shrink onto the glass material, also called vitreous body, the coefficient of thermal expansion of the main body must be greater than that of the glass material. Likewise, the glazed metal pin should not detach from the glass material during cooling, so that in turn the metal pin in known solutions has a lesser coefficient of thermal expansion than the glass material. If stainless steel is used as the material of the main body in igniters of personal safety devices, a metal pin made of nickel-iron or a nickel-iron alloy is usually glazed into the glass material.

Furthermore, the through opening is eccentrically arranged in the case of leadthroughs with more than one pin according to US 2007/0187934 A1.

Punching out the main bodies from a sheet material according to US 2007/0187934 A1 has disadvantages. One disadvantage of punching from a plate of material, for example, a sheet of the main body material, is that it produces its share of material waste.

DE 10 2010 045 624 A1 therefore proposes to manufacture the main body from a wire material by a cold forming process and to provide the main body with a release region so that the through-opening can also be punched out of the main body manufactured by a cold forming process.

DE 10 2006 056 077 A1 shows a pyrotechnic protection device, in particular, for an airbag or belt tensioner, with a through-opening in a main body, whereby the through-opening is punched into the main body.

Further writings from which metal fixing material leadthroughs are derived are, for example, EP 1 491 848 A1, EP 1 455 160 A1, EP 1 813 906 A1, EP 2 431 703 A1 or DE 10 2006 004036 A1.

In particular, in the case of metal fixing material leadthroughs with two metal pins, the through-opening into which at least one metal pin is inserted is, in most cases, eccentrically positioned. Eccentric openings can have disadvantages in an efficient series production.

No pin material has become known from any of the above-mentioned applications relating to metal fixing material leadthroughs which, in particular, after the metal pin has been glazed into the glass material, allows for a safe post-processing, for example, for assembly. The pin materials, especially NiFe, disclosed in WO 2012/110 245 A1, tend during rational series production in automated production plants and/or during further processing of the metal fixing material leadthroughs to an igniter and/or the assembly of the end product, i.e. when being pushed onto a connector, to lead to bending and, in extreme cases, even break through, so that, for example, unwanted rejects can be produced.

What is needed in the art is a way to avoid at least some of the disadvantages of the prior art and to provide a metal fixing material leadthrough with a conductor, characterized in that it can be produced in rational series production with a lower reject rate and/or that it can be assembled more safely, for example, when the end product is pushed onto or into a connector.

SUMMARY OF THE INVENTION

In some exemplary embodiments provided according to the present invention, a metal fixing material leadthrough for an igniter of at least one of airbags or belt tensioners includes: a main body having a through-opening formed therein; and at least one metal pin fused into a glass or glass-ceramic fixing material in the through-opening and having a core region. The at least one metal pin, at least in its core region, consists of stainless steel made to the EN 10020 standard, the stainless steel is selected in such a way that, when converted to a standard dimensioning of a metal pin diameter of 1.00±0.03 mm and a metal pin length of 11.68±0.02 mm, the at least one metal pin has a maximum elastic deflection $W_{max}$ of less than 0.24 mm.

In some exemplary embodiments provided according to the present invention, a metal fixing material leadthrough for an igniter of at least one of airbags or belt tensioners includes: a main body having a through-opening formed therein; and at least one metal pin fused into a glass or glass-ceramic fixing material in the through-opening and having a core region. The at least one metal pin, at least in its core region, consists of stainless steel made to the EN 10020 standard. A coefficient of thermal expansion $\alpha_{metal\ pin}$ at a temperature of 650° C. of the at least one metal pin falls in a range of $9 \times 10^{-6}$ 1/K to $15 \times 10^{-6}$ 1/K.

In some exemplary embodiments provided according to the present invention, a metal fixing material leadthrough for an igniter of at least one of airbags or belt tensioners includes: a main body having a through-opening formed therein, an upper side configured to face an explosive material and on which an ignition bridge can be or is attached, and an underside which is opposite the upper side; and at least one metal pin which is fused in the through-opening in a glass or glass-ceramic fixing material. The at least one metal pin and the main body are made of a compatible material combination in such a way that, at least one of when an ignition bridge is installed or when the upper side is covered with a conductive film, at least one of an anode reaction or a cathode reaction does not occur or occurs only to a small extent on the upper side of the main body.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1A:
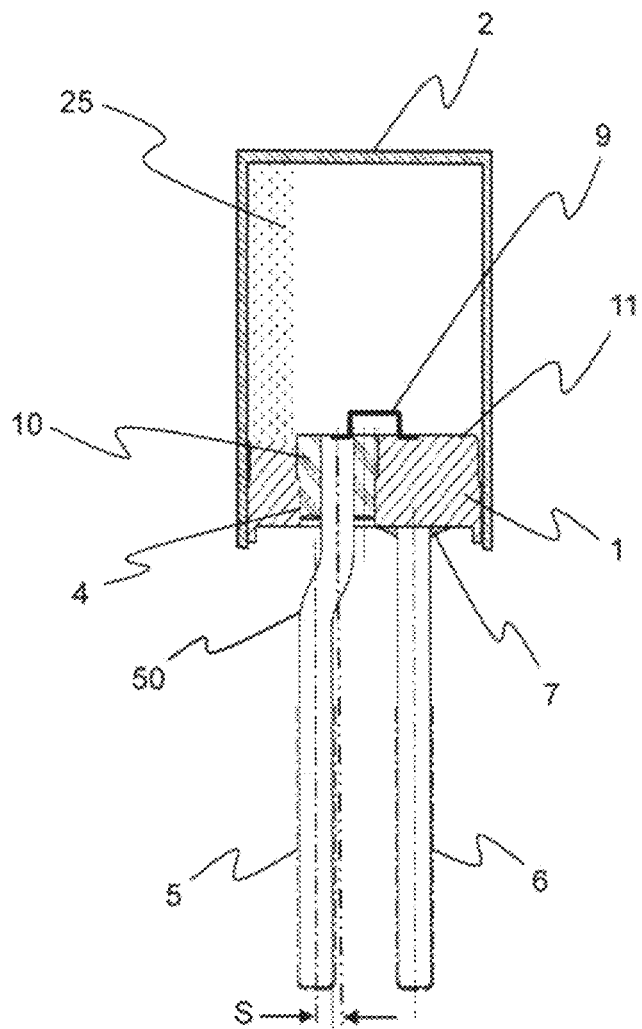
FIG. 1A illustrates a leadthrough provided according to the present invention inserted into an airbag igniter.

Exemplary embodiments provided according to the present invention provide a metal fixing material leadthrough with at least one metal pin, the at least one metal pin consists, at least in its core region, of a stainless steel according to the EN 10020 standard. The metal pin is characterized in that the stainless steel is selected in such a way that the metal pin, when converted to the standard dimensioning of a metal pin diameter of 1.00±0.03 mm and a metal pin length of 11.68±0.2 mm, has a maximum elastic deflection of less than 0.13 mm, less than 0.15 mm, less than 0.18 mm, less than 0.20 mm, or less than 0.21 mm. In some embodiments, the maximum elastic deflection is in the range of 0.01 to 0.26 mm.

Elastic deflection in the sense of the present invention is understood to be a deflection of the metal pin under which the metal pin at least substantially returns to its original shape when the mechanical load is removed. At least in substance, no plastic deformation takes place, or in other words, in the mentioned load range, the material of the metal pin is found to be in the range of the elastic deformation.

The metal pin length refers to the projection of the metal pin measured from the bottom side of the glazing and is therefore independent of the length of the glazing and/or the header thickness.

Since the metal pin is fused into a through-opening of a main body in a glass or glass-ceramic material, the metal pin is heated during glazing, usually to temperatures of 600° C. and more, such as 650° C. and more. It is then newly cooled down. This means that, following heating, the stainless steel of the metal pin is present in cooled state after the glazing process, which is generally referred to as annealed state. The material properties of the annealed stainless steel differ greatly from those of the raw state, i.e. the unannealed state.

The metal pin can be a solid material or a solid material with a coating. If it is a metal pin with a coating, the core region of the metal pin refers to the solid material, i.e. the stainless steel material surrounded by the coating.

Exemplary embodiments provided according to the present invention have the advantage that the stainless steel pin is characterized by low bendability, in particular, in the annealed state. This means that a greater mechanical load is required to deform it plastically than is the case with a nickel-iron pin used up to now. In other words, for a given mechanical load below the point of plastic deformation, the stainless steel pin remains elastically deformable. Among other things, this benefits the production process, since the probability of deformation of the stainless steel pin is decreased in production lines. Likewise, in post-processing, for example, during coating or during grinding of the ends, a more exact positioning of e.g. the tools can be achieved. It is also easier to push an unbent metal pin, i.e. one that does not deviate from the nominal dimensions, onto connectors or similar.

In some embodiments, the stainless steel is selected in such a way that, in a standard load test in the range of 3 N to 4 N, the metal pin shows a maximum deflection of 0.21 mm, i.e. the deflection is less than 0.21 mm. With such a small deflection, only an elastic deformation or distortion of the metal pin occurs, so that the metal pin returns to its original state.

The standard load test for this purpose is designed in such a way that a metal pin with the dimensions 1.00±0.03 mm and a metal pin length of 11.68±0.02 is subjected to the previously mentioned mechanical load, perpendicular to the pin axis, and the deflection is measured, for example, up to the limit $W_{max}$, at which the limit of elastic deflection is reached. If the metal pin has other dimensions, a corresponding metal pin in the dimensions of the standard load test must be manufactured or the deflection must be calculated accordingly.

In some embodiments, the metal pin provided according to the present invention is selected in such a way that the mechanical load 0.25% (strain) of the at least one metal pin corresponds to a stress of more than 450 MPa, such as more than 480 MPa or more than 500 MPa, or from 450 MPa to 700 MPa. These ranges are considered to be useful because, although high stress has a low bendability, i.e. also a higher limit of plastic deformation, materials with high stress are more difficult to post-process, for example to grind. These ranges are higher for annealed metal pins made of stainless steel than for annealed metal pins made of nickel-iron, as known from the state of the art.

Surprisingly, when using stainless steel as the pin material, it was found that the force required for extraction of the stainless steel metal pin from the glass material of the through-opening is more than 250 N, for example of 250 N to 400 N or of 300 N to 380 N. It is assumed that this is due to the fact that the glazed and thus annealed stainless steel metal pin is so hard that it better resists the pressure of the compression glass-to-metal sealing. In other words, and in simplified terms, if the main body shrinks onto the glass body in the leadthrough as described previously during cooling, the pressure continues through the glass body and presses on the metal pin. If the pin is soft, it can give way to this pressure, so that the clamping effect in the glass body is weaker than in the case of a harder metal pin. The clamping effect is an important aspect for the force required for extraction.

In some embodiments, the stainless steel metal pin is glazed in a main body. The main body can likewise be made out of a metal, such as steel, high-grade steel, stainless steel, titanium, a titanium alloy, magnesium, a magnesium alloy, an aluminum alloy, aluminum or AlSiC.

In some embodiments, the same material class is used for the material of the main body and for the material of the metal pin, such as the metal pin arranged in the fixing material, i.e. stainless steel metal pin and stainless steel main body or titanium metal pin and titanium or titanium alloy main body or vice versa etc. It has been recognized that the choice of the same class of materials can suppress possible electrochemical corrosion, which can be beneficial for production processes, such as for cleaning and/or galvanic coating, but can also contribute to the long-term durability of the end product, for example, an igniter.

In some embodiments, the stainless steel of the at least one metal pin is an alloyed stainless steel according to the EN 10020 standard, such as a chromium-containing stainless steel.

In some embodiments, the stainless steel is selected from the group made up of
 ferritic stainless steels
 precipitation-hardened stainless steels.

If necessary, martensitic stainless steels are also conceivable.

The fact that it is possible to achieve a leadthrough that is stable over the long term with glazed metal pins made of stainless steel is surprising, since stainless steel does not have the ratio of coefficients of thermal expansion described previously. In fact, the coefficients of thermal expansion of stainless steel are usually higher than those of the fixing material used for glazing, such as glass and/or glass-ceramic materials. The fact that greater extraction forces are required than with the nickel-iron pins, which actually fall into this ratio, is unexpected.

There are also useful regions here. For example, in some embodiments the stainless steel is selected in such a way that the coefficient of thermal expansion $\alpha_{metal\ pin}$, or CTE (P), at a temperature of 650° C., falls in the range of $9.0 \times 10^{-6}$/K to $15.0 \times 10^{-6}$/K, such as $11.0 \times 10^{-6}$/K to $14.0 \times 10^{-6}$/K, $11.5 \times 10^{-6}$/K to $14.0 \times 10^{-6}$/K or $11.0 \times 10^{-6}$/K to $13.5 \times 10^{-6}$/K, or $11.5 \times 10^{-6}$/K to $12.5 \times 10^{-6}$/K.

In some embodiments, the glassy or glass-ceramic fixing material has a coefficient of thermal expansion $\alpha_{glass}$ at a temperature up to Tg of the fixing material, such as the glass and/or glass-ceramic material, in the range of $4 \times 10^{-6}$ 1/K to $10.6 \times 10^{-6}$ 1/K. This thermal expansion circumstance may be advantageous in combination with the previously mentioned circumstance of thermal expansion of stainless steel.

In some embodiments, the main body has a coefficient of thermal expansion $\alpha_{main\ body}$ which is at least $2\times10^{-6}$ 1/K, such as $10\times10^{-6}$ 1/K greater than the coefficient of thermal expansion $\alpha_{glass}$ of the fixing material, for example $\alpha_{main\ body}$ is in the range of $11\times10^{-6}$ 1/K to $18\times10^{-6}$ 1/K. Especially in combination with one, or, in particular, both, of the previously mentioned coefficient of thermal expansion circumstances of the stainless steel and of the fixing material, a stable leadthrough, such as for compression glass-to-metal sealing, can be achieved to great advantage.

The stainless steel for the metal pin can be selected from the group of ferritic stainless steels, martensitic stainless steels, or precipitation-hardened stainless steels. Ferritic stainless steel may be useful in some applications, as it is efficient to manufacture and/or to supply into production facilities.

In some embodiments, the at least one metal pin has at least one bending point. In some embodiments, the metal pin is bent in such a way that there is an axial offset S of the region of the metal pin in the through-opening and of the connection region at the opposite end of the metal pin. This may be advantageous for realizing a through-opening located centrally in the main body.

In addition, a bent metal pin, such as an S-shaped bent metal pin, may be advantageous, in the case of the stainless steels used as material for the metal pin provided in accordance with the present invention, because it can provide a spring-like function when mounted on connectors, which, when pushed onto the connector, reduces the probability of damage to the connector system, e.g. pushing metal sleeves out of plastic holders. In addition, mechanical load peaks are prevented by the glass material of the leadthrough.

The bent metal pin is more difficult to produce with the stainless steels used according to the present invention than with the NiFe steels used up to now, since the bending takes place after annealing and, as can be seen from the strength properties described, the annealed stainless steel can only be plastically deformed by applying greater force.

In some embodiments, the metal fixing material leadthrough has at least one additional metal pin which is electrically conductively connected to the main body, such as by a soldered or welded joint. This creates a direct electrical contact of the main body with the second metal pin, so that a second through opening in the main body is not necessary.

In some embodiments, the metal pin, which is electrically conductively connected to the main body, consists at least in its core region of a non-stainless steel, such as NiFe, and is connected to the main body by a welded joint. This metal pin is in an unannealed state, at least in the portion away from the region of the welded joint which was heated during welding. This choice of material has the benefit that non-stainless steel in raw state is, as described, mechanically more resilient than annealed stainless steel. Thus, such embodiments can have the best mechanical strength properties. However, it is costlier to produce the welded joint than to solder the second metal pin to the main body.

In some embodiments, the further metal pin likewise has at least one bending point. The further metal pin may be bent in such a way that there is an axial offset between the region of the metal pin connected to the main body and the connection region at its opposite end.

In order to favor a soldering of the metal pin made of stainless steel with metallic solders, the at least one metal pin glazed into the through-opening and/or the electrically conductive metal pin connected to the main body has a nickel coating. In some embodiments, the nickel coating is present at least in the region of the glazing and/or in the region of the head surface of the metal pin in the glazing and/or in the region of the electrically conductive connection with the main body. In addition, or as an alternative to the nickel layer, a gold layer may also be provided.

In some embodiments, the gold layer is at least on top of the nickel layer in regions.

Thus, the nickel coatings are possible:
on the glazed metal pin in a region which is provided with a gold layer on at least regions of the nickel layer, such as in the connection region at the end of the metal pin
and/or
on the glazed metal pin in a region in contact with the fixing material,
and/or
on the metal pin which is electrically conductively connected to the main body in a region which is provided with a gold layer on at least regions of the nickel layer, such as in the connection region at the end of the metal pin,
and/or
on the metal pin, which is electrically conductively connected to the main body, in a region where the metal pin is connected to the main body by a metallic solder material.

To ensure a safe electrical connection, the at least one metal pin glazed in the leadthrough and/or the metal pin electrically conductively connected to the main body may be coated with gold, at least in some regions. In some embodiments, the gold layer is present at least in the connection region and/or the metal pin electrically conductively connected to the main body. The connection region is, for example, the region where the metal pin is inserted into, for example, a connector system and/or where it makes contact with contacts of a connector system.

In order to provide a metal fixing material leadthrough with a metal pin that is as easy to process or assemble as possible, the metal pin of such a metal fixing material leadthrough is designed in such a way that it breaks in the annealed state in a test system with a metal pin length L of 11.68 mm when vertically loaded at the end point L with a force $F_{max}$, where $F_{max}$ is more than 2.2 N. The metal pin may also be designed so that it is elastically deformable in the annealed state in a test system with a metal pin length L of 11.68 mm when vertically loaded at the end point L up to a maximum deflection $W_{max}$, where $W_{max}$ is more than 0.15 mm, such as from 0.15 mm to 0.4 mm. $W_{max}$ thereby denotes the limit of elastic deformation. If the load exceeds $W_{max}$, plastic deformation occurs, i.e. there is a permanent bending of the metal.

If a real metal pin has dimensions different than those specified for a test system, it is produced in the dimensions of the test system for comparison and/or its measurement results are converted so that they correspond to the dimensions of the test system.

The metal pin provided according to the present invention made of stainless steel has a much higher stiffness than a NiFe pin after glazing and heating to 600° C. or 650° C. This is due to the fact that NiFe softens due to the high temperature, whereas stainless steel does not. Thus, for example, stainless steel can be subjected to 50% more stress on the pin after smelting than NiFe.

Metal fixing material leadthroughs with metal pins made of stainless steel are characterized by a very high mechanical stability of the metal pin. The high mechanical stability prevents bending, such as permanent or plastic bending, of the metal pin during assembly and post-processing. The use of stainless steel as pin material ensures that, for example, the mechanical stability is greatly increased compared to pins made of a NiFe material.

Furthermore, the metal pin in a metal fixing material leadthrough for igniters of airbags and belt tensioners provided according to the present invention is characterized in that it unexpectedly requires a very high force for extraction, in excess of 250 N, such as 250 N to 400 N or 300 N to 380 N. This was surprising to the person skilled in the art, since the coefficient of thermal expansion of the pins made of a stainless steel fall in the range of $11.0\times10^{-6}$/K to $13.5\times10^{-6}$/K at 650° C. and thus in a range that is different from the glass material and the surrounding metal of the metal fixing material leadthrough, so that lower required forces for extraction were expected, which made the use of metal pins made of stainless steel appear to be disadvantageous.

It is assumed that this higher force required for extraction is due to better chemical adhesion of the pin in the glass material due to the chosen pin material.

In some embodiments, the stainless steel of the at least one metal pin is selected from the group of stainless steels whose transition point between elastic and plastic deformation in the annealed state is less than 50% below the transition point between elastic and plastic deformation in the raw state.

Such a selection ensures that the metal pin, after being inserted into the fixing material, such as into the glass material and inserted into the opening of the main body of the metal fixing material leadthrough, does not soften during the subsequent heating of the main body to at least 600° C. or 650° C., in such a way that the metal pin becomes plastically deformable under the mechanical loads that occasionally occur. An overly great reduction of the transition point from elastic to plastic deformation of the annealed metal pin would result in a considerable reduction of the stiffness of the metal pin and thus of the mechanical stability.

Whereas the transition point from elastic to plastic behavior of a ferritic stainless steel in the raw state is at a stress of 600 MPa and decreases to 500 MPa in the stress-strain diagram by heating to 600° C., the transition point of NiFe decreases from 700 MPa to 300 MPa in the stress-strain diagram by heating to 600° C. This means that the NiFe steels in the unannealed state are definitely mechanically more stable than the stainless steels provided according to the present invention. In the annealed state, however, the stainless steels are more resilient to mechanical stress and elastically deformable up to higher loads.

Since stainless steel in the annealed state softens less than NiFe, further mechanical processing of stainless steel is more difficult than with NiFe. This manifests itself in a more complex bending behavior such as if, for example, the S-shaped bending of the metal pins is to be produced, as well as a more difficult processing with regard to shaping the end of the metal pin or pins, such as, for example, grinding or stamping a radius. The person skilled in the art has been deterred from using stainless steel as the material for the metal pin instead of NiFe, in particular, because of the inappropriate position of the coefficients of thermal expansion and the difficulty of post-processing.

An advantage of stainless steel as a pin material when compared to conventional materials such as NiFe is that in combination with a stainless steel main body there is practically no galvanic corrosion when the bridge wire is connected or when electrically conductive films are applied. This is due to the fact that the difference in electrochemical potentials between the stainless steel main body and the stainless steel metal pin is small. The aim is to achieve an absolute value of the difference in electrochemical potentials between the metal pin, such as the glazed metal pin, and the main body of less than 0.3 V. This means that the absolute value of the difference between the electrochemical potentials of the metal pin, such as the glassed-in metal pin, and the main body may be in the range of 0 to 0.3 V. This means that practically no galvanic corrosion can occur. If, on the other hand, a NiFe pin is used, electrons migrate from the NiFe pin to the material of the main body, for example, austenitic stainless steel, and galvanic corrosion occurs. If, for example, ferritic stainless steel is used as the material for the metal pin, the electrical potential of the metal pin and the main body consisting of austenitic stainless steel is practically the same and galvanic corrosion does not occur, unlike with a NiFe pin.

The present invention also provides that the selection of materials for main body and/or metal pin can be based on the electrochemical potentials compared to seawater. This potential against seawater is a good measure for the evaluation of the resistance against electrochemical corrosion attacks, since in operating conditions, such as over long storage or operating periods, the films forming on the surface of the leadthrough can have corrosiveness similar to that with seawater.

Following this concept, when selecting materials for the main body and/or for the at least one metal pin, such as for the metal pin in the fixing material, for example stainless steels, it may be advantageous that their absolute values of the electrochemical potential in comparison to seawater amount to at most 0.36 V, i.e. correspondingly to a range of 0 to 0.36 V.

Since there is a very low difference in electrochemical potential between stainless steel as a pin material and stainless steel as a main body material, a metal fixing material leadthrough for igniters of airbags and/or belt tensioners with at least one metal pin, which is fused into a glass or glass-ceramic fixing material in a leadthrough of a main body can be provided, in which at least the metal pin and the main body are made of a compatible material combination, so that, when an ignition bridge is installed, an anode and/or cathode reaction is suppressed on the upper side of the main body. The upper side of the leadthrough is defined as the side of an ignition bridge to be installed and the underside is defined as the side of the electrical connections, i.e., the side of the metal fixing material leadthrough from which the metal pins protrude.

In some embodiments, at least one metal pin and the main body have essentially the same electrochemical potential, so that if the ignition bridge is installed, no electrons flow over the ignition bridge via a water film absorbed on the water surface. In some embodiments, the absolute value of the difference in electrochemical potential between the main body and the stainless steel pin is between 0.3 V and 0.0 V, i.e. the main body has, for example, a potential of 0.07 V, the metal pin a potential of 0.02 V, so that the difference amounts to 0.05 V and thereby there is as good as no electron flow over the ignition bridge from the metal pin to the main body and/or through conductive films.

In some embodiments, the Cr content in the stainless steel is in the range of 10 percent by weight to 30 percent by weight, such as 15 percent by weight to 25 percent by weight. For example, a 20 percent by weight chromium content results in a very low coefficient of linear expansion amounting to approximately $10\times10^{-6}$/K at 0 to 40° C. The low coefficient of expansion at 40° C. also correlates with a low coefficient of expansion at the glazing temperature, usually 600° C. or 650° C.

In order to enable soldering of the metal pin made of stainless steel, it is intended that the metal pin is provided, as described, with a Ni layer and/or a gold layer at least in some regions. The nickel layer can also be provided below the gold layer. A direct gold plating of the stainless steel pin without an intermediate nickel layer is also possible.

Surprisingly, it was found that when stainless steel is used as the material for the metal pin, a force required for extraction of the metal pin in the range of 250 N to 400 N, such as of 300 N to 380 N is provided by the glass material. This force required for extraction is unexpectedly about 50% higher than, for example, with a NiFe metal pin.

A particularly stable metal pin includes the metal fixing material leadthrough when the metal pin is designed in such a way that it breaks in the annealed state in a test system with a metal pin length L of 11.68 mm, when vertically loaded at the end point L with a force $F_{max}$, where $F_{max}$ is more than 2.2 N and/or where the metal pin is designed in such a way that it breaks in the post-heated state in a test system with the metal pin length L of 11.68 mm when acted upon vertically at the end point L at a maximum deflection $W_{max}$, the $W_{max}$ being more than 0.15 mm, such as from 0.15 mm to 0.4 mm. Such a stable metal pin is, for example, then formed when stainless steel, such as chromium-containing stainless steel, is used as the material for the metal pin.

Until now, persons skilled in the art have been discouraged from using stainless steels in pressure glass leadthroughs, for example, for use in igniters of airbags, because the coefficient of thermal expansion of these steels, at 11.0 to $13.5 \times 10^{-6}$/K at 650° C., is significantly higher than the coefficient of expansion of glass, which is in the range of 10.6 to $6.1 \times 10^{-6}$/K. It has been found that, surprisingly, despite the higher coefficient of expansion of the conductor, which is above the glass, going contrary to the state of the art, which stipulates that for glass-metal leadthroughs, the thermal expansion of the conductor must not be higher than that of the glass used, in order to provide a sufficient seal, even if the coefficient of expansion of the metal pin is greater than that of the glass, a sealed glazing is provided when a positive joint pressure is exerted on the glass by the main body. In some embodiments, the joint pressure is greater than 30 MPa, such as greater than 50 MPa or greater than 100 MPa. With such joint pressures, reliable glazing is achieved. The joint pressure is the pressure at the point of transition of the main body to the glass material. In compression glass-to-metal sealing, it usually acts perpendicularly from the inner wall of the leadthrough on the glass body. It is a substantial factor for the forces required for extraction of the glass body from the main body.

A higher joint pressure is provided when sufficient compressive pre-stress is applied to the glass by the main body as external conductor. The resulting joint pressure between the glass and the inner conductor is generated when the leadthrough cools down after smelting. If this joint pressure is clearly positive, i.e. greater than 30 MPa or greater than 50 MPa, such as greater than 100 MPa, the transition between glass and metal, i.e. the transition from glass to the metal pin, remains closed and thus sealed, even though the coefficient of expansion of the metal pin is greater than that of the glass.

The joint pressure depends directly on the difference in strain between glass and the surrounding metal. Furthermore, dependencies on the geometry are also conceivable. In some embodiments, the area of the main body outside the through-opening is larger than the area of the through-opening itself. The joint pressure is a surface pressure. The joint pressure expresses the force with which a first body presses on a second one per unit of area.

To apply the necessary joint pressure, the difference between the coefficient of expansion of the main body and the coefficient of expansion of the glass is at least 2 ppm/K, such as at least 4 ppm/K, whereby the coefficient of expansion $\alpha_{main\ body}$ is higher than the coefficient of expansion of the glass $\alpha_{glass}$. In some embodiments, the coefficient of expansion of the metal pin $\alpha_{metal\ pin}$ is chosen in such a way that the coefficient of expansion of the metal pin is 1.1 times greater than the coefficient of expansion $\alpha_{glass}$ of the glass. In some embodiments, the coefficient of expansion is in the range 1.1 $\alpha_{glass}$ to 2 $\alpha_{glass}$.

In order to apply the necessary pressure of the main body on the glass material and to guarantee the seal, the main body may be made of nickel-free, stainless, chemically resistant steel (high-grade steel).

It may be advantageous if the main body, which can also be an external conductor, is an austenitic stainless steel that is characterized by good weldability.

In addition to a straight metal pin, it can also be provided that the metal pin of the metal fixing material leadthrough is not straight but bent.

The fixing material of the metal fixing material leadthrough is a glass or glass ceramic material. The coefficient of expansion of the glass materials used $\alpha_{glass}$ is in the range of $4 \times 10^{-6}$/K to $10.6 \times 10^{-6}$/K, such as of $6.1 \times 10^{-6}$/K to $10.6 \times 10^{-6}$/K.

The main body of the metal fixing material leadthrough into which the metal pin is glazed includes an opening as, for example, described in EP 1 813 906 A1, EP 1 455 160 A1 or EP 2 431 703 A1, which can be obtained in different ways. One possibility is a cold forming process as described in EP 2 431 703 A1, where the opening is made in the body by punching.

In the case of pressure glass leadthroughs, such as those used to ignite airbags and belt tensioners, the material of the main body is selected in such a way that the coefficient of expansion $\alpha_{main\ body}$ is greater than that of the glass material, in such a way that pressure is applied to the glass material, resulting in compression glass-to-metal sealing. A main body made of austenitic stainless steel with a coefficient of expansion of $\alpha=18.3 \times 10^{-6}$/K may be advantageous for compression glass-to-metal sealing.

A further aspect of the present invention is to provide a metal fixing material leadthrough, such as for igniters of airbags and/or belt tensioners, in which galvanic corrosion occurs only to a small extent. This aspect is solved in that the at least one metal pin and the main body of the leadthrough are made of a compatible material combination in such a way that, if an ignition bridge is installed or if the top side is covered with a conductive film, an anode and/or cathode reaction does not occur or occurs only to a small extent on the top side of the main body.

In some embodiments, the at least one metal pin and the main body have an electrochemical potential and the absolute value of the difference between the electrochemical potentials of the metal pin and the main body is at most 0.3 V. In some embodiments, the electrochemical potentials of metal pin and main body are essentially the same. In some embodiments, the absolute value of the difference between the electrochemical potentials of the metal pin and the main body is in the range of 0.1 V to 0.0 V, such as of 0.05 V to 0.0 V. The absolute value of the difference of the electrochemical potential of the metal pin and/or the main body compared to sea water may be at most 0.36 V and is, for example, in the range of 0.36 V to 0.0 V.

The at least one metal pin, for example, consists at least in its core region, just like at least on its upper side of the main body, of a stainless steel according to the EN 10020 standard.

In some embodiments, the stainless steel of the metal pin and the main body are selected in such a way that the stainless steel of the metal pin and the main body form a passivation film on their surface, such as instead of an absorbed water film.

In some embodiments, the at least one metal pin consists, at least in its core region, of a stainless steel according to the EN 10020 standard, whose coefficient of thermal expansion $\alpha_{metal\ pin}$ at a temperature of 650° C. is in the range of 9 to 15, such as of $11.0\times10^{-6}$/K to $14.0\times10^{-6}$/K, of $11.5\times10^{-6}$/K to $14.0\times10^{-6}$ 1/K or of $11\times10^{-6}$/K to $13.5\times10^{-6}$ 1/K, for example of $11.5\times10^{-6}$/K to $12.5\times10^{-6}$ 1/K.

The glass or glass-ceramic fixing material may exhibit a coefficient of thermal expansion $\alpha_{glass}$ at a temperature up to Tg of the fixing material in the range of $4\times10^{-6}$ 1/K to $10.6\times10^{-6}$ 1/K.

In some embodiments, the main body has a coefficient of thermal expansion $\alpha_{main\ body}$, that is at least $2\times10^{-6}$ 1/K, such as $10\times10^{-6}$ 1/K higher than the coefficient of thermal expansion $\alpha_{glass}$ of the glass, for example in the range of $11\times10^{-6}$ 1/K to $18\times10^{-6}$ 1/K.

The stainless steel of the at least one metal pin is, for example, an alloyed stainless steel according to the EN 10020 standard, such as a chromium-containing stainless steel. The stainless steel may be selected from the group of ferritic stainless steels and/or precipitation-hardened stainless steels. The force required for extraction of the metal pin from the glass material of the leadthrough may be more than 250 N, such as 250 N to 400 N or 300 N to 380 N.

In some embodiments, the main body consists of a metal, such as steel, stainless steel, high-grade steel, titanium, a titanium alloy, magnesium, a magnesium alloy, an aluminum alloy, aluminum, or that substantially comprising these. In some embodiments, the main body is made of stainless steel of the types 316, 317, 302, 304, 321, 317, 430, 410 and/or 416.

The metal pin, converted, such as to the standard dimensioning of a metal pin diameter of 1.00±0.03 mm and a metal pin length of 11.68±0.2 mm, comprises a maximum elastic deflection $W_{max}$ of less than 0.13 mm, less than 0.15 mm, less than 0.18 mm, less than 0.20 mm, or less than 0.24 mm, such as in the range of 0.01 to 0.26 mm.

The metal pin, which is electrically conductively connected to the main body, consists, for example, at least in its core region, of a non-stainless steel, which may be made of NiFe, and wherein this metal pin is connected to the main body by a welded joint.

In some embodiments, the at least one metal pin glazed in the through-opening and/or the metal pin electrically conductively connected to the main body is coated with nickel. In some embodiments, the nickel layer is present in regions of the metal pins, selected from the group including combinations of the same:
- on the glazed metal pin in a region which is provided with a gold layer on at least regions of the nickel layer, such as in the connection region at the end of the metal pin,
- on the glazed metal pin in a region in contact with the fixing material,
- on the metal pin which is electrically conductively connected to the main body in a region which is provided with a gold layer on at least regions of the nickel layer, such as in the connection region at the end of the metal pin,
- on the metal pin, which is electrically conductively connected to the main body, in a region where the metal pin is connected to the main body by a metallic solder material.

Alternatively, or additionally, it can be provided that the at least one metal pin glazed in the through-opening and/or the metal pin that is electrically conductive with the main body is coated with gold. In some embodiments, the gold coating is present at least in the connection region of the metal pin and/or the metal pin electrically conductively connected to the main body, which is opposite the end of the respective metal pin located in and/or on the main body.

Referring now to the drawings, FIG. 1A shows an axial section of an exemplary implementation of a metal fixing material leadthrough 1, which may be for use in an igniter or ignition device of an airbag or other personal protection equipment such as belt tensioners, as described, for example, in EP 2 270 417 A1. The metal fixing material leadthrough includes, without limitation, two metal pins 5, 6, which are designed as metal pins provided according to the present invention and include a stainless steel as the material of the metal pin. The metal fixing material leadthrough has a main body 1, to which one of the two parallel metal pins 5 and 6 is electrically connected. The two metal pins 5 and 6 are arranged parallel to each other in the embodiment shown. One of them functions as a conductor, while the second is connected to ground. In the case shown, the first metal pin 5 functions as a conductor and the metal pin 6 as a ground pin. The ground pin 6 is electrically connected to the main body 1, for example, by a solder connection 7 using a solder material. The width of the two metal pins is usually between 0.98 and 1.05 mm, such as 1.0 mm.

At least one of the metal pins, such as the metal pin 5 acting as conductor, is guided through the main body 1. For this purpose, the metal pin 5 is fused over part of its length into a fixing material 10, such as a glass plug cooled from a glass melt. The metal pin 5 protrudes on at least one side beyond the front side of the glass plug 10, usually on the underside of the main body, and, in the embodiment shown, is flush with the second front side of the glass plug 6 after completion of production, this second front side being in the same plane as the surface 11 of the main body 1. For this purpose, the metal pin 5 can be arranged in the through-opening 4 during smelting in such a way that it initially protrudes beyond the main body 1. After smelting or casting, the metal pin 5 and, if necessary, the protruding cooled fixing material 10 can be ground off so that this and/or these are flush with the front side of the glass plug 10 and the surface 11 of the main body 1. Other variants are also conceivable. Smelting of the metal pin into the glass material and of the glass material into the main body is usually done at temperatures of 600° C. or 650° C. and more, depending on the glass material used. Due to the higher coefficient of thermal expansion of the material of the main body $\alpha_{main\ body}$ ~$18.3\times10^{-6}$/K when compared to the glass material $\alpha_{glass}$ material in the range of $4\times10^{-6}$/K to $10.6\times10^{-6}$/K, the main body exerts a pressure on the fixing material, in particular the glass material, after cooling down and a compression glass-to-metal sealing is provided. On the other hand, heating also affects the mechanical stability of the metal pin. It is in this manner that the metal pins generally soften when exposed to temperature. It has been recognized that in the leadthrough application, stainless steel does not soften as much as NiFe when exposed to temperature. Precious metal pins remain much more resilient to bending than the NiFe pins used in current leadthroughs.

In the case shown, the ground pin 6 is fastened directly to the back of the main body 1, for example, by solder material 7. Usually, this is metallic solder material. The ground pin 6, like the glazed metal pin 5, can also be made of a stainless steel according to the present invention, such as a chromium-containing stainless steel.

The main body 1 can be designed as a punched part. A punched part exists if at least the through-opening 4, for example also the final geometry of the main body 1, is produced by punching. In some embodiments, the geometry describing the outer contour, such as the outer circumference of the main body 1, can also be produced by cutting out, for example punching. The punched part can either be further employed maintaining the geometry as it was after the punching process, or, in a further work step, which may follow directly after the punching process, it can be further formed, e.g. embossed or deep-drawn. Alternatively, it is also possible to obtain the entire main body by a cold forming process as described in EP 2 431 703 A1.

The through-opening 10 provided for receiving and fixing the metal pin 5 by the glass plug 10 is created by a punching process in the form of a hole. Subsequently, the metal pin 5 at the back 11 of the main body 1 of the metal fixing material feed-through is inserted into the through-opening 4 together with the glass plug 10 and the metal body containing the glass plug 10 and the metal pin 5 is heated to approximately 600° C., so that after a cooling process, the metal shrinks and thereby a frictional connection between glass plug 10 with metal pin 5 and the main body 1 is formed, also called compression glass-to-metal sealing. Due to the difference in the coefficients of thermal expansion of the main body 1 and the glass material of the glass plug 10, this compression glass-to-metal sealing can be provided.

It is also conceivable to introduce the fixing material 10, in an alternative design, in a molten or flowable state, for example, to introduce the glass melt from the front side into the through-opening. During cooling, a form-fitting and material-locking connection is then created between the outer circumference of the metal pin 5 and the inner circumference of the through-opening 4. The main body 1 can be designed in such a way that the relationship between the thickness of the main body 1 and the maximum expansion of the through-opening 4, perpendicular to the axial direction of the through-opening 4 is in the inclusive range of 0.5 to 2.5.

It should be emphasized that the present invention can also be developed with insulation materials, which are not based on glass materials, in the leadthrough 4.

FIG. 1A shows the installation of a metal fixing material leadthrough in an igniter component, for example, an airbag igniter. In addition to the metal fixing material leadthrough, in which the metal pin 5 is glazed, the igniter component includes an igniter cap 2, which holds the explosive 25 for the igniter component, i.e. the airbag igniter. The explosive 25 is triggered by an electrical impulse from the bridge wire 9. The bridge wire 9 connects the glazed metal pin 5 with the main body 1 which is connected to ground. Contrary to the drawing which shows the bridge wire 9 schematically and for clarification, the bridge wire 9, as a rule, lies on the surface of the main body 1 and/or the fixing material 10.

FIG. 1A also clearly shows the bending point 50 of the glazed metal pin, which leads to an axial offset S of the region of the metal pin 5, which is glazed into the through-opening and leads to the connection region of the metal pin.

The offset is selected in such a way that the metal pins of the metal fixing material leadthrough can, for example, be inserted into connector systems. Usually the two metal pins 5, 6 are arranged and/or bent in such a way that in the overall view there is a central arrangement of both metal pins 5, 6 in relation to the main body 1.

Figure 1B:
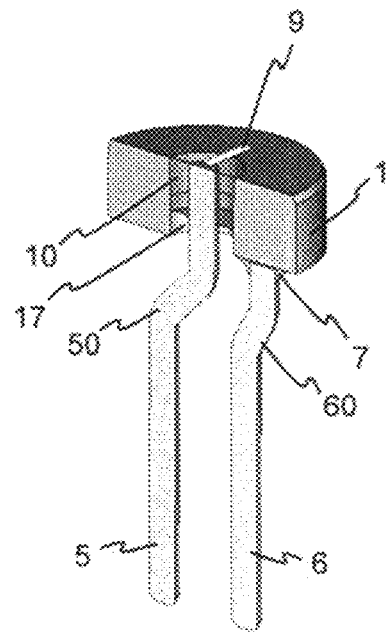
FIG. 1B illustrates a metal fixing material leadthrough with a metal pin provided according to the present invention.

FIG. 1B shows a sectional view of the metal fixing material leadthrough inserted in the igniter cap 2, comprising the main body 1 with the metal pins 5, 6. The same components as in FIG. 1A are assigned the same reference numbers. In contrast to the embodiment shown in FIG. 1A, in the implementation according to FIG. 1B, the ground pin 6 also has a bending point 60, so that there is an axial offset of the region of the metal pin connected to the main body 1 and its connection region at the opposite end. The bridge wire 9, between main body 1 and metal pin 5 is clearly visible in FIG. 1B. In contrast to the stamped main body from FIG. 1A, the main body in FIG. 1B is a cold-formed main body according to EP 2431703 A1, with a release region 17. The opening 10 is also stamped out of the cold-formed main body after insertion of the release region 17 as in EP 2431703 A1.

Figure 2:
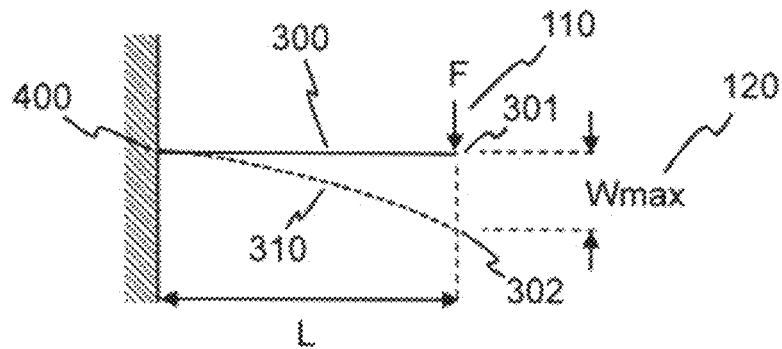
FIG. 2 illustrates a test setup for determining the bending stiffness.

FIG. 2 shows a measurement arrangement or test system for determining the bending strength of the metal pins. FIG. 2 shows a clamped metal pin 300, with a length L=11.68 mm and a diameter of 1.0 mm, on which a force F, marked 110, acts, in Newton (N).

In the test system or measurement arrangement as shown in FIG. 2, 400 is the wall in which the pin is clamped, 300 is the pin with the length L and 301 is the end point of the metal pin in the unloaded state. The bent, i.e. the loaded, pin is designated 310 and the end point of the bent pin is designated 302. The difference between the end points 301 and 302 designates the maximum deflection $W_{max}$.

Applying a force of 6.380 N will result in a deflection of 0.345 mm for a NiFe metal pin in its raw state. At higher forces and higher deflection, the elastic deformation changes into an irreversible plastic deformation. In the cases of plastic deformation at forces greater than 6.380 N and/or deflections greater than 0.345 mm, the pin may also break.

If the NiFe pin has been heated, for example, to a glazing temperature of 650° C., the deflection is 0.105 mm when a force of only 1.933 N is applied to the metal pin after cooling (annealing). In contrast with the embodiment shown in FIG. 1, at forces greater than 1.933 N and deflections greater than 0.105 mm, the elastic deformation changes to plastic deformation in the annealed state as described above with respect to the raw condition. This consideration of the forces applied shows that the NiFe pin loses a great deal of mechanical stability when heated.

In contrast to this, when using a stainless steel, for example, a ferritic stainless steel, such as AlSi 430, plastic deformation occurs only at forces greater than 4.976 N and bends $W_{max}$ exceeding 0.269 mm in the raw state and above 3.984 N and/or bends $W_{max}$ exceeding 0.216 mm in the annealed state. This demonstrates that after heat treatment, for example, at 650° C., the mechanical stability and/or the achievable maximum deflection of the ferritic stainless steel pin (AlSi 430) in the test system is approximately 100% higher than that of a NiFe 47 pin.

In these examples, the values given for $W_{max}$ represent the limit values at which an elastic deflection of the metal pin is still present. If the mechanical load in these examples is increased above the limit values mentioned, there is of course a bending beyond the values of $W_{max}$ mentioned, but this is then a plastic bending, i.e. irreversible.

In practice, this means that due to the glazing process, e.g. at temperatures of 650° C., the stainless steel pin is much more resilient to bending than the NiFe 47 pin, which softens much more. With stainless steel, a material is therefore provided that allows a metal pin to be designed in such a way that in the post-heated, i.e. annealed state in a test system with a metal pin length L of 11.68 mm, it is only plastically deformed at the end point when vertically loaded with a force $F_{max}$ exceeding 2.5 N, such as exceeding 3 N, exceeding 3.2 N or 3.5 N, in this example 3.984 N.

This also means that the maximum elastic bending and/or deflection $W_{max}$ in the test system mentioned may be greater than 0.15 mm, such as in the range of 0.15 mm to 0.3 mm and/or 0.4 mm.

Thus, the probability of the metal pin being damaged under mechanical stress in post-processing, for example when bending forces are applied in the assembly, is significantly reduced by exemplary embodiments provided according to the present invention.

Figure 3A:
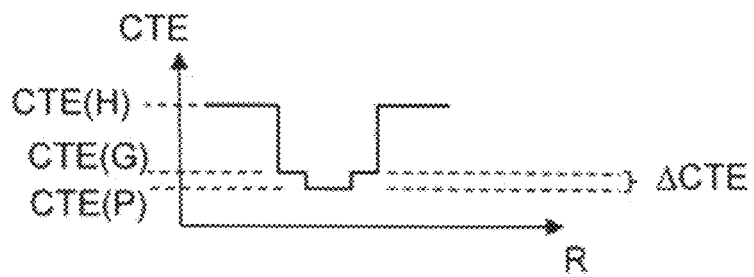
FIG. 3A illustrates the coefficients of expansion of glass, main body, and metal pin in a known metal fixing material leadthrough.
Figure 3B:
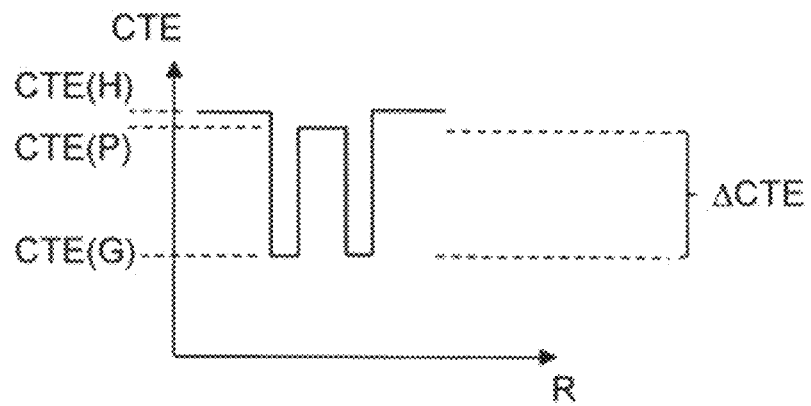
FIG. 3B illustrates the coefficients of expansion of glass, main body, and metal pin in a metal fixing material leadthrough provided according to the present invention.

FIG. 3A and FIG. 3B show the difference in the coefficients of expansion for conventional leadthroughs and for the leadthrough according to the present invention.

FIG. 3A shows the coefficients of expansion of conventional metal fixing material leadthroughs. Here CTE (H) is the coefficient of expansion of $\alpha_{main\ body}$ or the header, CTE (G) is the coefficient of expansion of the fixing material $\alpha_{glass}$ and CTE (P) is the coefficient of expansion of the metal pin $\alpha_{metal\ pin}$, which is arranged in the fixing material. As FIG. 3A shows, in order to provide compression glass-to-metal sealing, the coefficient of expansion of the main body (CTE (H)) is significantly greater than the coefficient of expansion (CTE (G)) of the fixing material, such as glass. For example, the coefficient of expansion CTE (H) of the main body is in the range of $18.3 \times 10^{-6}$/K in the case where austenitic stainless steel is used as the material of the main body. The coefficient of expansion of the glass material (CTE (G)), which is also referred to as $\alpha_{glass}$, is usually in the range of $4 \times 10^{-6}$/K to $10.6 \times 10^{-6}$/K and thus significantly lower than the coefficient of expansion CTE (H) of the main body. In the state of the art, the coefficient of expansion CTE (P) of the metal pin was always lower than that of the surrounding glass material, even if only slightly. Until now, it was assumed that this was necessary to achieve a permanent fixing material leadthrough, because otherwise the metal pin could detach from the glass in the event of thermal fluctuations. Therefore, metal pins made of non-stainless steels, especially NiFe, are used for this application.

FIG. 3B shows the coefficients of expansion for a stainless steel pin provided according to the present invention. As shown in FIG. 3B, the coefficient of expansion of the metal pin (CTE (P)) is lower than that of the main body (CTE (H)), but higher than the coefficient of expansion CTE (G) of the fixing material. Whereas the stainless steels have coefficients of expansion in the range of 11.0 to $13.5 \times 10^{-6}$/K, the coefficient of expansion of the fixing material, e.g. glass, is usually only in the range of $4 \times 10^{-6}$/K to $10.6 \times 10^{-6}$/K, such as $6.1 \times 10^{-6}$/K to $10.6 \times 10^{-6}$/K and thus below the coefficient of expansion of the metal pin. Although the coefficient of expansion of the metal pin is thus greater than that of the glass material, contrary to the state of the art as shown in FIG. 3A, sufficient sealing and compression glass-to-metal sealing can also be provided for the metal pin made of stainless steel provided according to the present invention with $\alpha_{metal\ pin} > \alpha_{glass}$ if a positive joint pressure is exerted on the glass by the main body with the coefficient of expansion $\alpha_{main\ body}$ or CTE (H). In the case of a high joint pressure exerted by the main body on the glass material and the metal pin, the transition between glass and metal, such as the transition from the glass to the metal pin, remains closed and the seal is guaranteed. In particular, hermetic sealing can also be achieved. A sufficiently high joint pressure can be achieved if, in the top view, the area of the main body minus the area of the leadthrough is at least 1.2 times the area of the leadthrough.

Figure 4:
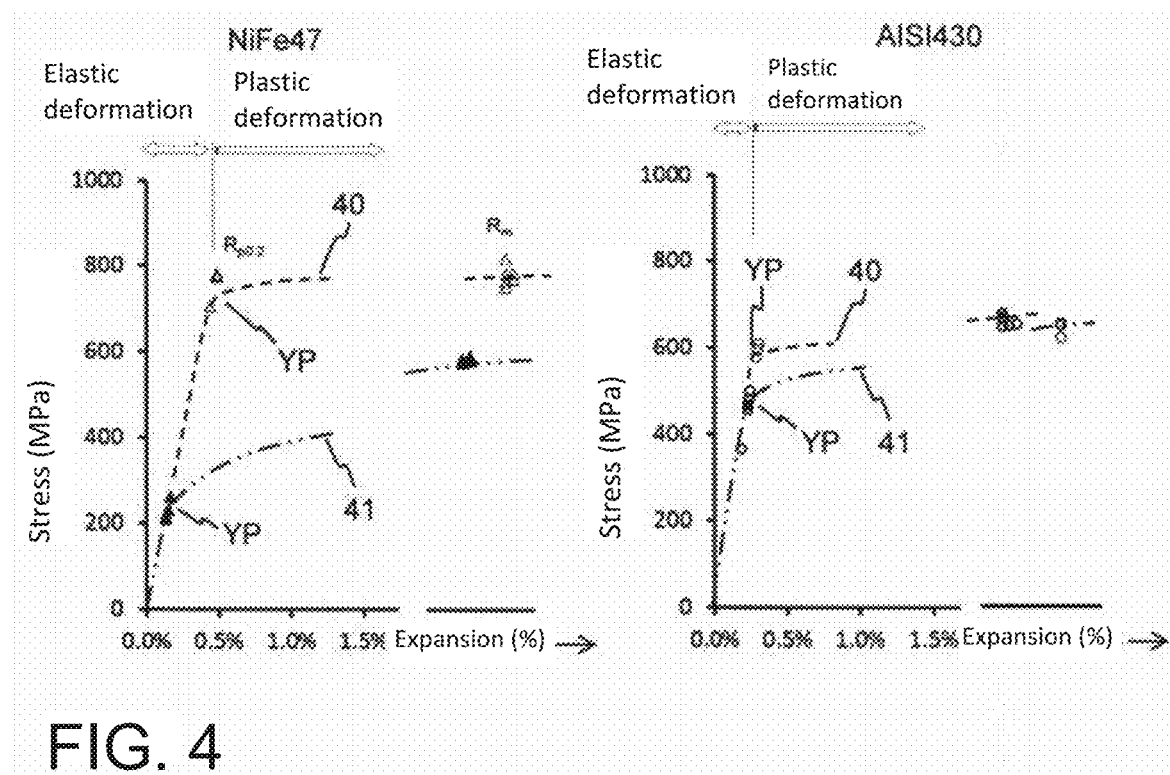
FIG. 4 illustrates the stress/strain curve for NiFe and stainless steel (AlSi 430), both heated and not heated.

FIG. 4 shows the stress-strain curve for a stainless steel pin according to the present invention and, for comparison, a stress-strain curve for a NiFe pin (NiFe 47). As FIG. 4 clearly shows, the NiFe pin loses much of its stability and is weakened compared to the stainless steel pin (AlSi430), such as a ferritic stainless steel pin, after heating, e.g. to 650° C. as required for glazing. This is how, in the case of AlSi430 ferritic stainless steel, the point of transition from elastic deformation to plastic deformation at approximately 0.25% strain shifts only from a stress of about 600 MPa for the raw material to 500 MPa for the annealed material, i.e. the stress at the transition point decreases only by about 20%. In contrast, the transition point from elastic to plastic deformation, when heated, shifts from a stress of 700 MPa to 200 MPa at about 0.25% strain in the case of the NiFe metal pin, i.e. the transition point of the raw material is 3.5 times higher than that of the annealed material. This shows the superiority of stainless steel material over NiFe as pin material for systems where the metal pin is in a thermally treated, especially annealed, state. This is all the more remarkable since the strength of the NiFe metal pin in the untreated, i.e. not heat-treated, state is by all means higher than that of the stainless steel pin, so that, in addition to the more suitable thermal expansion described above, it should be assumed that, for this reason as well, the previous non-stainless steel pins seemed to be more suitable.

Figure 5:
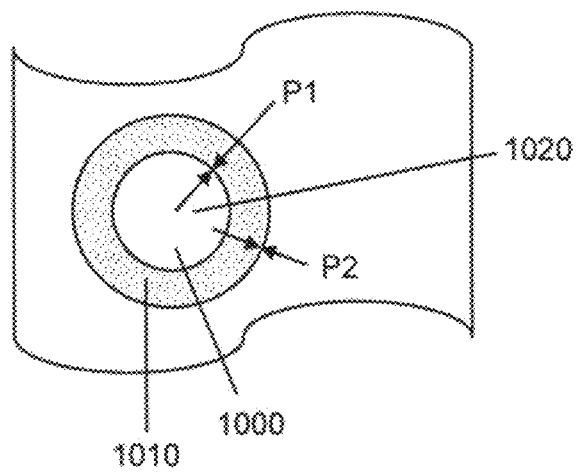
FIG. 5 illustrates a top view of a housing component with an opening and a metal pin glazed into the opening.

FIG. 5 shows a top view of a housing component, where the housing component comprises an opening 1000, into which a pin 1020 has been glazed into a glass material 1010. FIG. 5 also shows the joint pressure P1 of the glass material on the metal pin 1020 and the joint pressure P2 of the main body or housing component on the glass material. For the case in which the coefficient of expansion of the metal pin is greater than that of the glass material, it is necessary, according to the present invention, that sufficient compressive pre-stressing of the main body or housing component must be applied to the glass to ensure sufficient sealing. This is achieved, for example, if the geometry specification described previously is observed.

Figure 6:
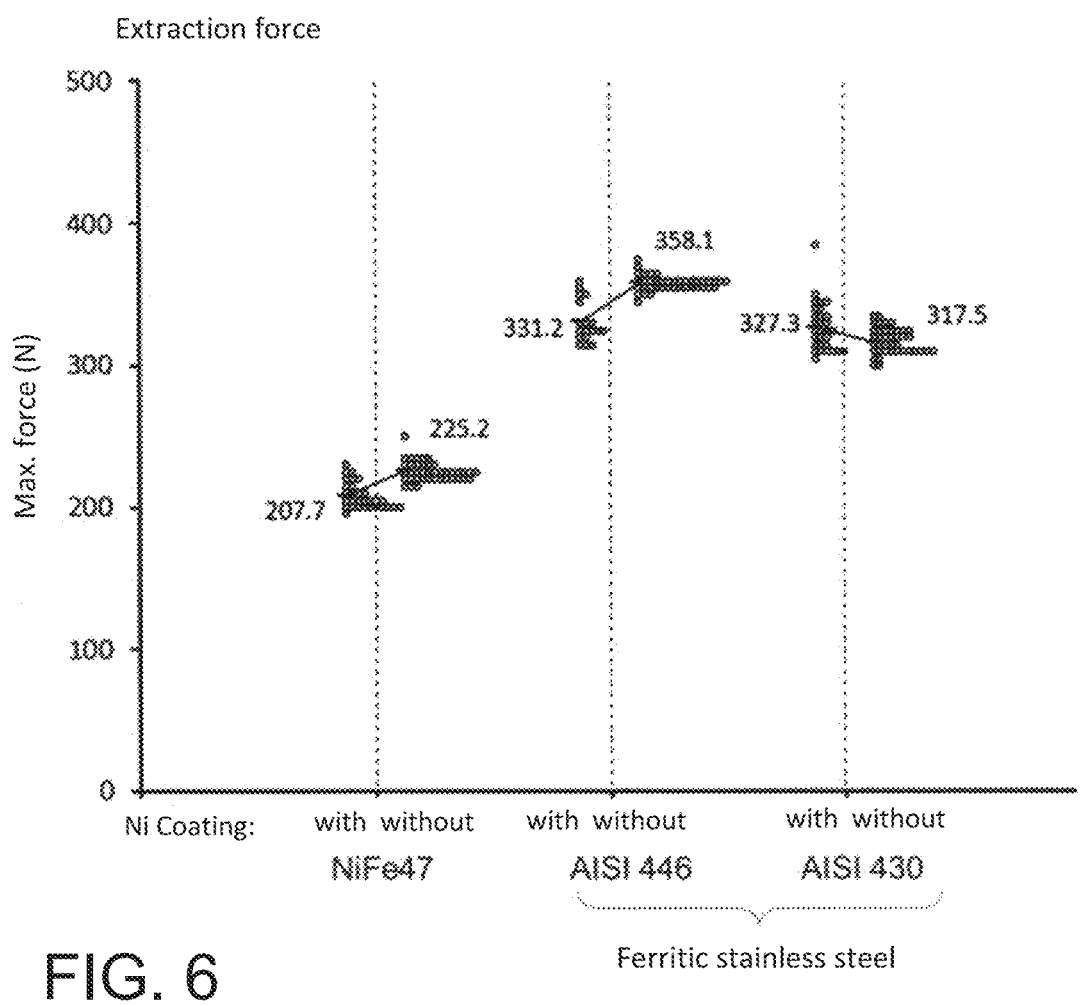
FIG. 6 illustrates forces required for extraction for metal pins made of NiFe/stainless steel.

FIG. 6 shows that, surprisingly, up to 50% higher forces are required for extraction with a stainless steel pin when compared to a previously used metal pin made of nickel-containing iron material (NiFe 47) by using a stainless steel material. As shown in FIG. 6, the forces required for extraction for NiFe 47 are only 207.7 N for a non-coated material and 225.2 N for a nickel coated NiFe 47 pin.

Surprisingly, much higher forces are required for extraction with the metal pin, provided according to the present invention, made of a stainless steel material, such as ferritic stainless steel. This is particularly surprising since, as explained, the situation of the coefficients of thermal expansion is rather unfavorable for the stainless steel pin. For the AlSi 446 ferritic stainless steel material, forces required for extraction of 331.2 N are achieved without a nickel coating, and 358.1 N with a nickel coating. The forces required for extraction are somewhat lower for the AlSi 430 stainless steel, where the force required for extraction is 317.5 N without nickel coating and 327.3 N with nickel coating. This shows that the metal pins made of stainless steel are not only characterized by higher mechanical strength when compared to conventional NiFe pins, but also by higher forces required for extraction. It can be assumed that the improved resistance against extraction of the metal pin made of stainless steel are due to the fact that the material of the metal pin remains harder than that of the NiFe pin after heating, so that the stainless steel can, so to speak, resist the joint pressure, that the header transmits to the metal pin via the glass, with more force and less indentation.

The nickel coating, or the gold coating, or a gold coating over a nickel coating, on one or more of the metal pins, in addition to requiring higher forces for extraction, serves to ensure that the metal pins can easily be put into contact.

Figure 7:
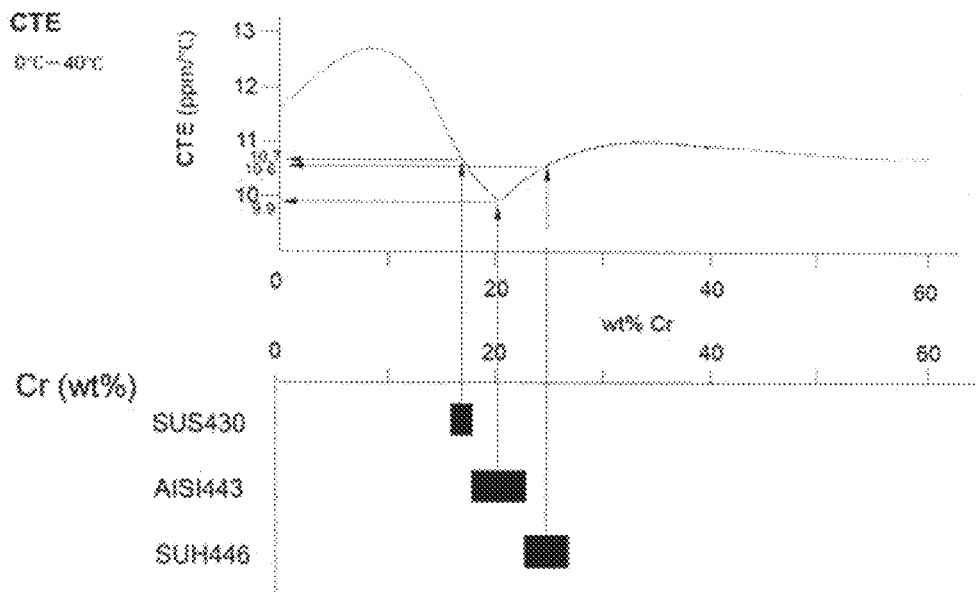
FIG. 7 illustrates the dependence of the coefficients of expansion of stainless steels on the Cr content.
Figure 8:
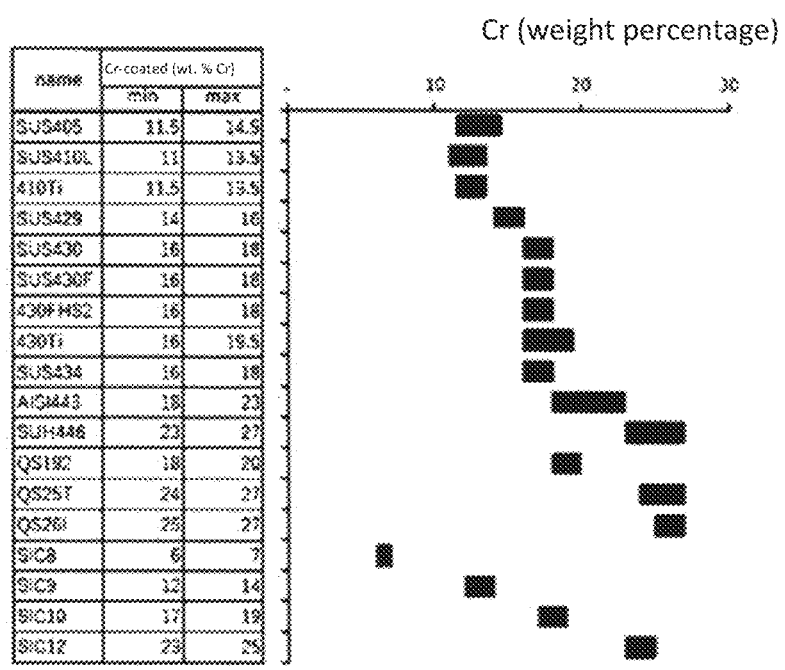
FIG. 8 illustrates the minimum and maximum chromium contents of various materials.

FIG. 7 shows the effect of the chromium content of the stainless steel on the coefficient of thermal expansion α or CTE (P) of stainless steel, as employed for the metal pin. The linear coefficient of thermal expansion is given from 0-40° C. in ppm/° C., i.e. ×10$^{-6}$/K, for a chromium content of 0-60 percent by weight. As can be seen from FIG. 7, for a chromium content of approximately 20% by weight, a coefficient of thermal expansion of $9.9 \times 10^{-6}$/K is achieved for an AlSi 443 stainless steel. In general, it can be seen that the CTE is dependent on the chromium content. From FIG. 7 it can be seen that a local minimum of CTE is achieved at a chromium content of approximately 20 percent by weight. An exemplary stainless steel for the metal pin is therefore chosen so that its chromium content falls in a range around the local minimum of the CTE, such as a chromium content in the range of 10 percent by weight to 30 percent by weight, which may be a chromium content in a range of 14 percent by weight to 28 percent by weight. The SUS430, AlSi443 and SUH446 stainless steels fall in this range and may be used as the material of the metal pin. The same applies to AlSi 446 and AlSi 430. The minimum and maximum chromium contents of various materials are illustrated in FIG. 8.

As will be explained further herein, materials with these chromium contents or chromium equivalent contents may also have advantages with regard to the electrochemical potential.

Figure 9:
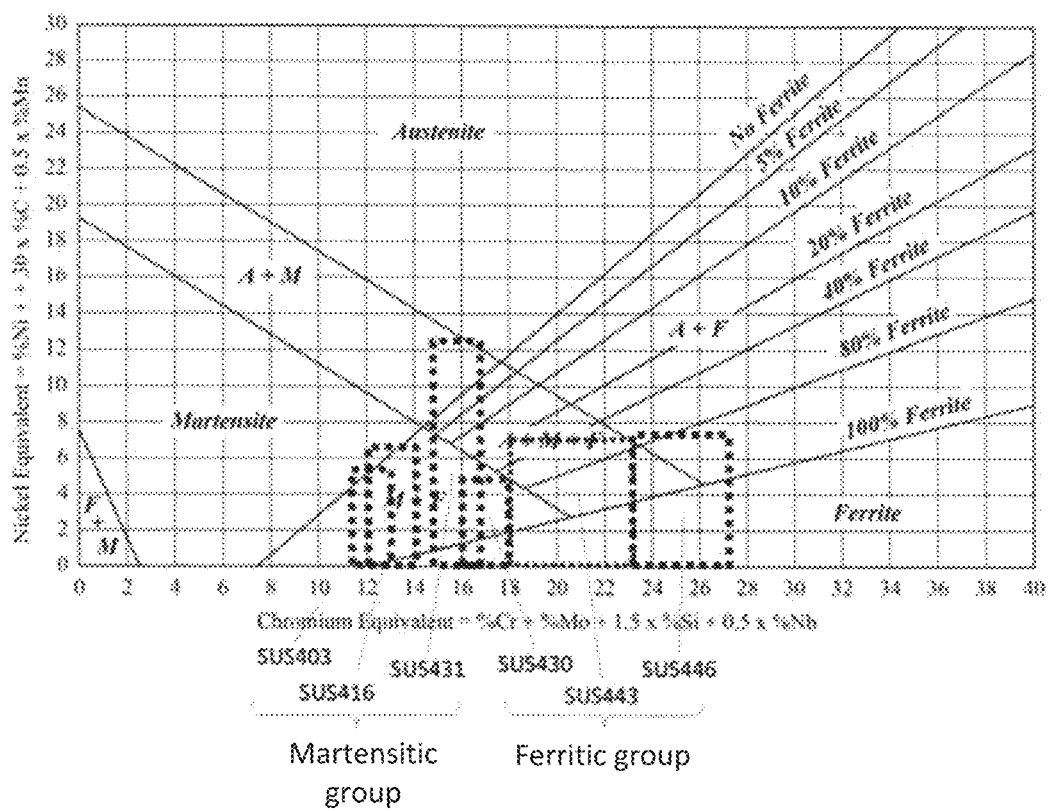
FIG. 9 illustrates the chromium and nickel equivalents for stainless steels.

FIG. 9 shows the chromium and nickel equivalents for martensitic and austenitic stainless steels.

The chromium equivalent, which includes not only chromium but also molybdenum, silicon, and niobium, is given for both martensitic and ferritic stainless steels. The chromium equivalent is in the range of 10 to 30 percent by weight, such as in the range of 12 percent by weight to 28 percent by weight. Exemplary advantageous areas in the sense of the present invention are marked by broken lines in FIG. 9.

In general, it can be said that a stainless steel, provided according to the present invention, comprises or is a chromium alloyed steel or features a chromium equivalent, the chromium equivalent being % Cr+% Mo+1.5×% Si+0.5×% Nb. The chromium equivalent usually gives a measured value for the total ferrite-forming elements of an austenitic stainless steel alloy, according to the empirical formula of Schaeffler and DeLong. Exemplary preferred areas of the chromium equivalents are those outlined in FIG. 9.

Figure 10A:
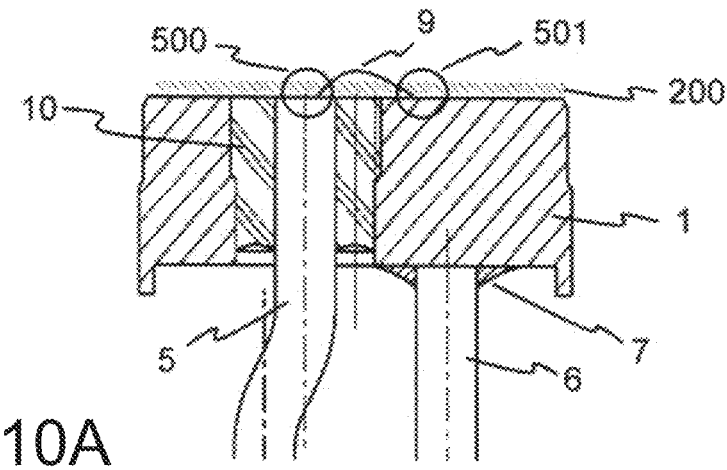
FIG. 10A illustrates the head of a metal fixing material leadthrough with bridge wire.
Figure 10B:
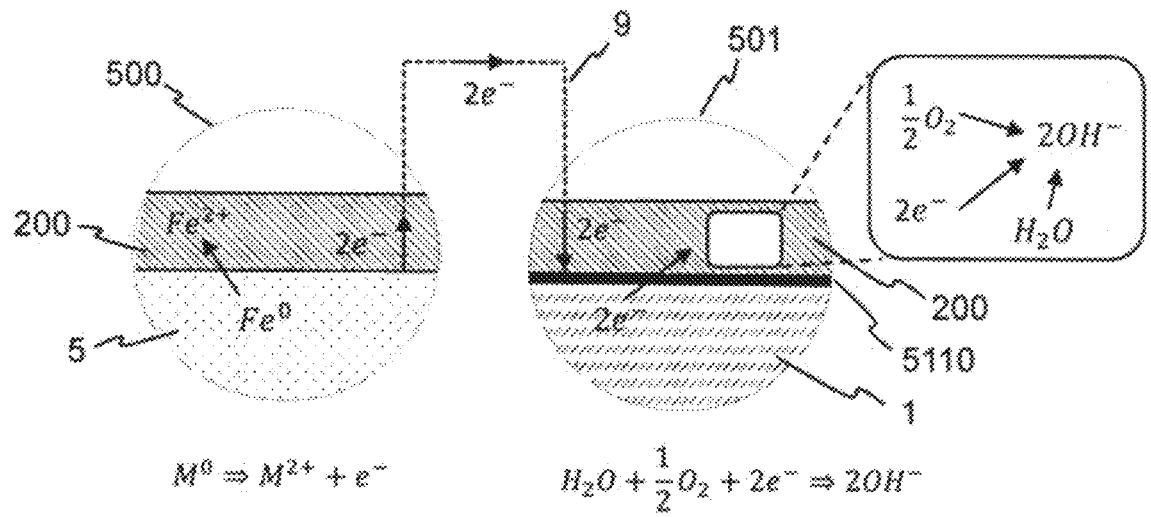
FIGS. 10B-10C illustrate the chemical reaction due to different electrochemical potentials in the prior art and according to the present invention.
Figure 10C:
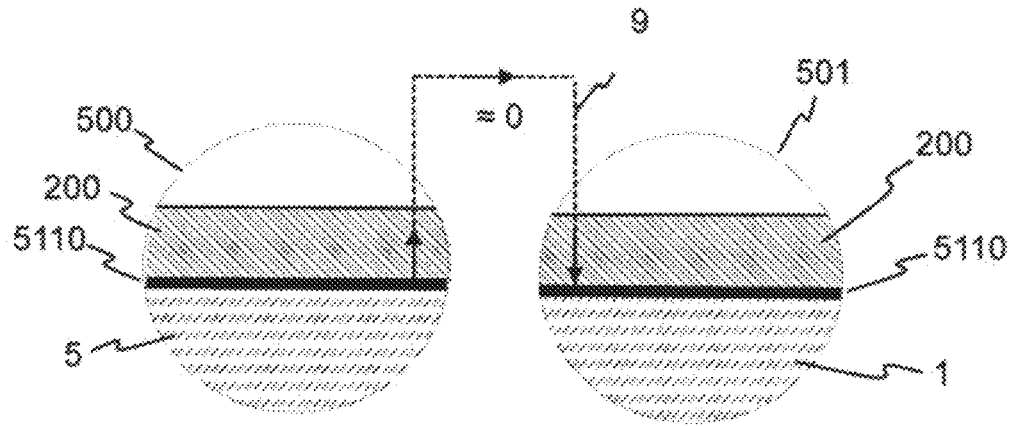

FIG. 10A shows the head part of a metal fixing material leadthrough provided according to the present invention and FIGS. 10B and 10C show the schematic diagram of the electrochemical reactions in the region of the metal fixing material leadthrough due to different electrochemical potentials in the state of the art (FIG. 10B) and according to the present invention (FIG. 10C).

FIG. 10A first shows the head part of a glass-metal fixing material leadthrough provided according to the present invention, as shown in FIG. 1A and FIG. 1B. The same components as in FIG. 1A and FIG. 1B have the same reference numbers. As can be seen in FIG. 10A, a conductive film, e.g. a water film 200, can form on the surface of the main body 1, so that if the electrochemical potential of the main body and the metal pin is different, an electron flow from the metal pin to ground, in this case the main body 1, occurs, which can cause oxidation of the metal pin and/or the main body and/or even the fixing material, e.g. the glass material. The flow of electrons from the metal pin to the main body is via the bridge wire 9. The electrically conductive film 200 can, for example, be present in the long-term operation of a generic leadthrough and play a role in the long-term stability of and corrosion attacks on the leadthrough. The electrons flow via the bridge wire 9 from the head of the metal pin 500 to the main body 501 or, if necessary, in the opposite direction, depending on the difference in potential. The insulating material between the main body and the metal pin is usually a non-conductive fixing material, such as a glass or glass ceramic material. The glass or glass-ceramic material in which the metallic conductor is glazed is marked 10. The metal pin passed through the opening bears the reference number 5, the metal pin soldered to the main body by a solder material 7 bears the reference number 6.

FIG. 10B shows the electron flow from the metal pin to the main body due to different electrochemical potentials. This corresponds to the state of the art. The difference in electrochemical potential between a metal pin made of a non-stainless steel, in particular NiFe, and the main body thus amounted to more than 0.3 V in the state of the art. Due to this difference in the electrochemical potential, an electrically conductive layer on the metal pin and the main body, e.g. a water film 200, can cause a conversion of iron to $Fe^{2+}$ and the release of two electrons which have migrated to the main body due to the existing electrical connection. In the presence of water, with oxygen, 2 OH$^-$ are formed as shown in FIG. 10B, i.e. the water film becomes increasingly basic and the material of the metal pin oxidizes to $Fe^{2+}$. The same reference numbers as in FIG. 10A are also identically assigned in FIG. 10B. Thus 500 denotes the region of the metal pin, 501 the region of the main body. The flow of electrons from the metal pin to the main body is via the bridge wire 9 or even via the electrically conductive film 200, in particular when the same becomes more and more basic as the reaction progresses. The increasing alkalinity of the film 200 can intensify the corrosion attack on the metals and even the glass material. The layer 5110 on the main body made of stainless steel is a passivation layer that forms on the stainless steel and may, in particular, contain oxygen. With NiFe as the pin material, it has been observed that a local cell can form between this passivation layer 5110 and the metal pin made of non-stainless steel, in particular, those made of NiFe. The difference in electrochemical potential between NiFe as pin material and e.g. AlSi 304L as material of the main body is 0.38 V. This can lead to electrochemical corrosion.

Whereas, in the state of the art, the metal pin can thereby corrode, according to the present invention this is no longer possible or at least is strongly suppressed, since the metal pin has substantially the same electrochemical potential in the region 500 as the main body with the reference number 501. As in FIG. 10C, there is no electron flow from the metal pin to the main body, even if the main body and metal pin are coated with an electrically conductive film 200, such as a water film. The surface 5110 of the main body and, for example, the metal pin are on stainless steel forming passivation layers, which may contain oxygen but do not oxidize further. Likewise, no increasingly alkaline water film is formed.

With AlSi 430 as the material of the glazed metal pin and AlSi 304 as the material of the main body, the absolute value of the difference in electrochemical potential is 0.02 V. Electrochemical corrosion attacks are hereby, at least, very strongly suppressed.

The same components as in the previous figures are assigned the same reference numbers. In some embodiments, the absolute value of the difference in the electrochemical potential of the main body and the stainless steel pin of the component according to the present invention is only 0.3 V to 0.0 V, such as 0.1 V to 0.0 V or 0.05 V to 0.0 V.

Figure 11:
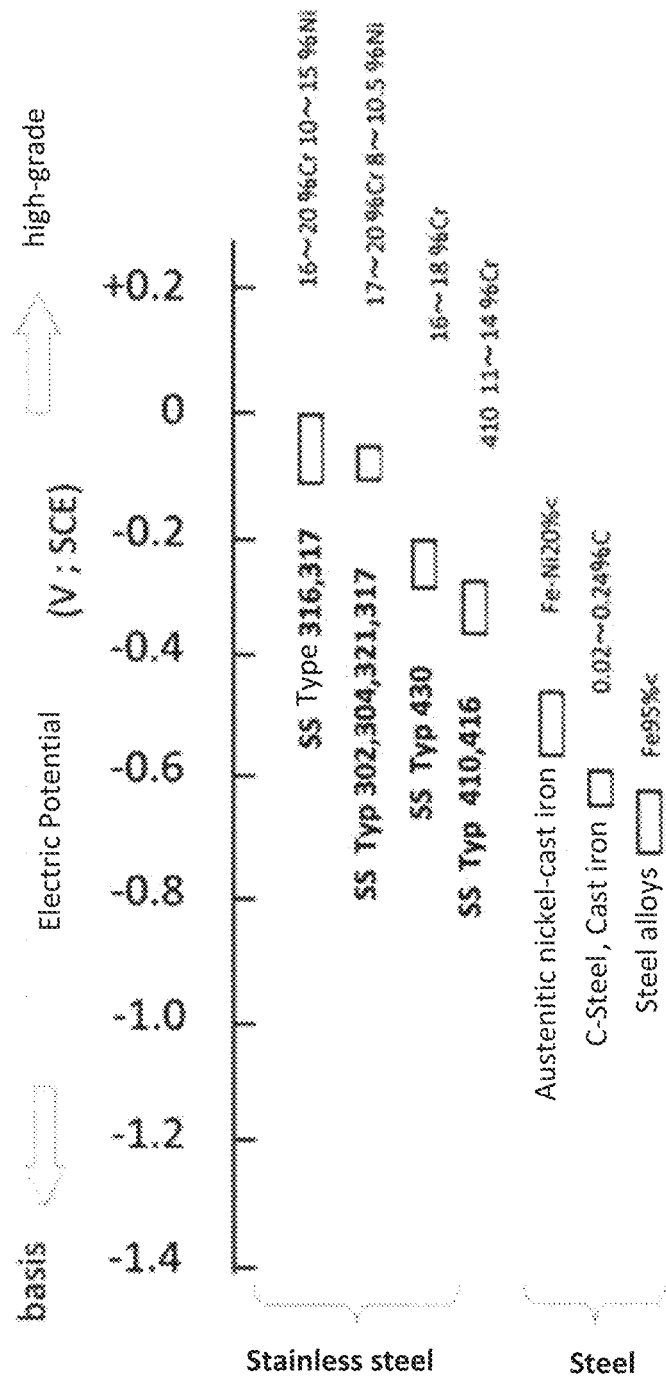
FIG. 11 illustrates electrochemical potentials of a selection of materials.

FIG. 11 shows the situation of the electrochemical potentials of a selection of possible materials, in particular stainless steels for the metal pin(s) and/or also for the main body. As described previously, good corrosion resistance depends on a suitable material combination of main body and metal pin in the fixing material. When selecting the material, the aim is to achieve the lowest possible difference in potential. However, the material of the main body must also meet other requirements. For example, it must be weldable to the metal cap 2, such as by laser welding. The manufacturing process of the main body is also an aspect, for example if it is punched or cold formed. Copper content can be beneficial for cold-formed main bodies.

The materials listed in FIG. 11 as stainless steels may be advantageous when selecting the metal pins 5, 6, such as the metal pin 5 arranged in the fixing material, and also for the selection of the material of the main body. These are the (AlSi) stainless steel types 316, 317, 302, 304, 321, 317, 430, 410 and/or 416, all of which are characterized by a low difference of electrochemical potential compared to seawater, in particular an absolute value of less than 0.4 V, such as less than 0.36 V, which, as described, is a good measure for assessing the resistance to galvanic corrosion attacks for the entire leadthrough.

The present invention thus initially specifies a metal fixing material leadthrough which is characterized on the one hand by a higher mechanical stability, such as in the case of metal pins being bent and/or requiring higher forces for extraction of the metal pins, and advantageously also by a lower susceptibility to corrosion, such as in adverse application conditions.

Due to improved mechanical stability, assembly errors can be reduced, which is reflected in improved reliability and/or reduced scrap. The improved corrosion resistance contributes to the long-term stability and thus to the safety of the equipment in which exemplary embodiments provided according to the present invention are used. The efficiency of the production of objects containing the leadthrough provided according to the present invention, as well as their safety, can thereby be increased overall.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A metal fixing material leadthrough for an igniter of at least one of airbags or belt tensioners, the metal fixing material leadthrough comprising:
   a main body having a through-opening formed therein and an upper side; and
   at least one metal pin fused into a glass or glass-ceramic fixing material in the through-opening and having a core region, the at least one metal pin, at least in its core region, and the main body, at least on its upper side, are made out of stainless steel made to the EN 10020 standard, the stainless steel of the at least one metal pin and of the main body is selected in such a way that the stainless steel of the at least one metal pin and of the main body form a passivation film on its surface, wherein the at least one metal pin and the main body are made of a compatible material combination in such a way that, at least one of when an ignition bridge is installed or when the upper side is covered with a conductive film, at least one of an anode reaction or a cathode reaction does not occur or occurs only to a small extent on the upper side of the main body, wherein the stainless steel of the at least one metal pin is selected in such a way that, when converted to a standard dimensioning of a metal pin diameter of 1.00±0.03 mm and a metal pin length of 11.68±0.02 mm, the at least one metal pin has a maximum elastic deflection $W_{max}$ of at least 0.13 mm.

2. The metal fixing material leadthrough of claim 1, wherein the stainless steel is selected in such a way that, at a mechanical load in the range of 3 N to 4 N, a deflection of at most 0.21 mm occurs.

3. The metal fixing material leadthrough of claim 1, wherein a mechanical load 0.25% (strain) of the at least one metal pin corresponds to a stress of more than 450 MPa.

4. The metal fixing material leadthrough of claim 1, wherein a force required for extraction of the at least one metal pin from the fixing material of the through-opening is more than 250 N.

5. The metal fixing material leadthrough of claim 1, wherein the main body is made of or substantially comprises at least one of a metal, steel, high-grade steel, stainless steel, titanium, a titanium alloy, magnesium, a magnesium alloy, an aluminum alloy, aluminum or AlSiC.

6. The metal fixing material leadthrough of claim 1, wherein the stainless steel of the at least one metal pin is selected in such a way that a coefficient of thermal expansion $\alpha_{metal\ pin}$ at a temperature of 650° C. of the at least one metal pin falls in a range of $9\times10^{-6}$ 1/K to $15\times10^{-6}$/K.

7. The metal fixing material leadthrough of claim 1, wherein the glass or glass-ceramic fixing material has a coefficient of thermal expansion $\alpha_{glass}$ at a temperature of up to Tg of the fixing material in a range of $4\times10^{-6}$ 1/K to $10.6\times10^{-6}$ 1/K.

8. The metal fixing material leadthrough of claim 1, wherein the main body has a coefficient of thermal expansion $\alpha_{main\ body}$, that is at least $2\times10^{-6}$ 1/K higher than a coefficient of thermal expansion $\alpha_{glass}$ of the fixing material.

9. The metal fixing material leadthrough of claim 1, wherein the at least one metal pin has at least one bending point.

10. The metal fixing material leadthrough of claim 1, further comprising at least one further metal pin electrically conductively connected to the main body.

11. The metal fixing material leadthrough of claim 10, wherein the at least one further metal pin that is electrically conductively connected to the main body has a core region, at least in its core region, is made of a non-stainless steel, and is connected to the main body by a welded joint.

12. The metal fixing material leadthrough of claim 10, wherein the at least one further metal pin has at least one bending point.

13. The metal fixing material leadthrough of claim 10, wherein at least one of the at least one metal pin glazed in the through-opening or the at least one further metal pin that is electrically conductively connected with the main body is plated with nickel.

14. The metal fixing material leadthrough of claim 10, wherein at least one of the at least one metal pin glazed in the through-opening or the at least one further metal pin electrically conductively connected to the main body is plated with gold.

15. A metal fixing material leadthrough for an igniter of at least one of airbags or belt tensioners, the metal fixing material leadthrough comprising:
a main body having a through-opening formed therein and an upper side; and
at least one metal pin fused into a glass or glass-ceramic fixing material in the through-opening and having a core region, the at least one metal pin, at least in its core region, and the main body, at least on its upper side, are made out of stainless steel made to the EN 10020 standard, the stainless steel of the at least one metal pin and of the main body is selected in such a way that the stainless steel of the at least one metal pin and of the main body form a passivation film on its surface, wherein the at least one metal pin and the main body are made of a compatible material combination in such a way that, at least one of when an ignition bridge is installed or when the upper side is covered with a conductive film, at least one of an anode reaction or a cathode reaction does not occur or occurs only to a small extent on the upper side of the main body, wherein a coefficient of thermal expansion $\alpha_{metal\ pin}$ at a temperature of 650° C. of the at least one metal pin falls in a range of $9\times10^{-6}$ 1/K to $15\times10^{-6}$ 1/K.

16. The metal fixing material leadthrough of claim 15, wherein the fixing material has a thermal expansion coefficient $\alpha_{glass}$ at a temperature of up to Tg of the fixing material in a range of $4\times10^{-6}$ 1/K to $10.6\times10^{-6}$ 1/K.

17. The metal fixing material leadthrough of claim 15, wherein the main body has a coefficient of thermal expansion $\alpha_{main\ body}$ that is at least $2\times10^{-6}$ 1/K higher than a coefficient of thermal expansion $\alpha_{glass}$ of the fixing material.

18. The metal fixing material leadthrough of claim 15, wherein the stainless steel of the at least one metal pin is an alloyed stainless steel according to the EN 10020 standard.

19. The metal fixing material leadthrough of claim 15, wherein the stainless steel of the at least one metal pin is a chromium alloyed steel or has a chromium equivalent, wherein the chromium equivalent is % Cr+% Mo+1.5×% Si+0.5×% Nb.

20. The metal fixing material leadthrough of claim 15, wherein the stainless steel has at least a chromium content or a chromium equivalent of between 10% by weight to 30% by weight.

21. The metal fixing material leadthrough of claim 15, wherein a force required for extraction of the at least one metal pin out of the fixing material of the through-opening amounts to more than 250 N.

22. The metal fixing material leadthrough of claim 15, wherein the main body is made of or substantially comprises at least one of a metal, steel, high-grade steel, stainless steel, titanium, a titanium alloy, magnesium, a magnesium alloy, an aluminum alloy, aluminum or AlSiC.

23. The metal fixing material leadthrough of claim 15, wherein the stainless steel is selected so that the at least one metal pin, when converted to a standard dimensioning of a metal pin diameter of 1.00±0.03 mm and a metal pin length of 11.68±0.02 mm, has a maximum elastic deflection $W_{max}$ of at least 0.13 mm.

24. The metal fixing material leadthrough of claim 15, wherein the at least one metal pin has at least one bending point.

25. The metal fixing material leadthrough of claim 15, further comprising at least one further metal pin having a core region and, at least in its core region, consisting of a material electrically conductively connected with the main body by a soldered joint or a welded joint.

26. The metal fixing material leadthrough of claim 25, wherein the at least one further metal pin that is electrically conductively connected to the main body, at least in its core region, is made of a non-stainless steel and is connected to the main body by a welded joint.

27. The metal fixing material leadthrough of claim 25, wherein the at least one further metal pin has at least one bending point.

28. The metal fixing material leadthrough of claim 15, wherein at least one of the at least one metal pin glazed in the through-opening or the at least one further metal pin electrically conductively connected to the main body is plated with nickel.

29. The metal fixing material leadthrough of claim 15, wherein at least one of the at least one metal pin glazed in the through-opening or the at least one further metal pin electrically conductively connected to the main body is coated with gold.

30. A metal fixing material leadthrough for an igniter of at least one of airbags or belt tensioners, the metal fixing material leadthrough comprising:
a main body having a through-opening formed therein, an upper side configured to face an explosive material and on which an ignition bridge can be or is attached, and an underside which is opposite the upper side; and
at least one metal pin which is fused in the through-opening in a glass or glass-ceramic fixing material, wherein the at least one metal pin and the main body are made of a compatible material combination in such a way that, at least one of when the ignition bridge is installed or when the upper side is covered with a conductive film, at least one of an anode reaction or a cathode reaction does not occur or occurs only to a small extent on the upper side of the main body, wherein the at least one metal pin comprises a core region and the at least one metal pin, at least in its core region, and the main body, at least on its upper side, are made out of a stainless steel according to the EN 10020 standard, wherein the stainless steel of the metal pin and of the main body is selected in such a way that the stainless steel of the metal pin and of the main body form a passivation film on its surface.

31. The metal fixing material leadthrough of claim 30, wherein the at least one metal pin and the main body each exhibit an electrochemical potential and an absolute value of a difference between the electrochemical potentials of the at least one metal pin and the main body amount to at most 0.3 V.

32. The metal fixing material leadthrough of claim 31, wherein the absolute value of the difference of the electrochemical potential of the at least one metal pin and of the main body each fall in a range of 0.1 V to 0.0 V.

33. The metal fixing material leadthrough of claim 31, wherein the absolute value of a difference in the electrochemical potential of at least one of the at least one metal pin or the main body with respect to seawater amounts to at most 0.36 V.

34. The metal fixing material leadthrough of claim 30, wherein the at least one metal pin comprises a core region and the at least one metal pin, at least in its core region, consists of stainless steel made to the EN 10020 standard, wherein a coefficient of thermal expansion $\alpha_{metal\ pin}$ of the at least one metal pin, at a temperature of 650° C., falls in a range of $9\times10^{-6}$/K to $15\times10^{-6}$/K.

35. The metal fixing material leadthrough of claim 30, wherein the fixing material has a coefficient of thermal expansion $\alpha_{glass}$ at a temperature of up to Tg of the fixing material in a range of $4\times10^{-6}$ 1/K to $10.6\times10^{-6}$ 1/K.

36. The metal fixing material leadthrough of claim 30, wherein the main body has a coefficient of thermal expansion $\alpha_{main\ body}$ that is at least $2\times10^{-6}$ 1/K higher than a coefficient of thermal expansion $\alpha_{glass}$ of the fixing material.

37. The metal fixing material leadthrough of claim 30, wherein the at least one metal pin comprises stainless steel and the stainless steel of the at least one metal pin is an alloyed stainless steel according to the EN 10020 standard.

38. The metal fixing material leadthrough of claim 30, wherein a force required for extraction of the at least one metal pin from the fixing material of the through-opening amounts to more than 250 N.

39. The metal fixing material leadthrough of claim 30, wherein the main body is made of or substantially comprises at least one of a metal, steel, stainless steel, high-grade steel, titanium, a titanium alloy, magnesium, a magnesium alloy, an aluminum alloy, aluminum, or stainless steel of at least one of the types 316, 317, 302, 304, 321, 317, 430, 410 or 416.

40. The metal fixing material leadthrough of claim 30, wherein the at least one metal pin comprises a core region and, at least in its core region, consists of stainless steel made to the EN 10020 standard, wherein the at least one metal pin, when converted to a standard dimensioning of a metal pin diameter of 1.00±0.03 mm and a metal pin length of 11.68±0.2 mm, shows a maximum elastic deflection $W_{max}$ of at least 0.13 mm.

41. The metal fixing material leadthrough of claim 30, further comprising at least one further metal pin electrically conductively connected to the main body and having a core region, the at least one further metal pin that is electrically conductively connected to the main body, at least in its core region, is made of a non-stainless steel and is connected by a welded joint with the main body.

42. The metal fixing material leadthrough of claim 41, wherein at least one of the at least one metal pin glazed in the through-opening or the at least one further metal pin electrically conductively connected with the main body is coated with nickel.

43. The metal fixing material leadthrough of claim 41, wherein at least one of the at least one metal pin glazed in the through-opening or the at least one further metal pin electrically conductively connected with the main body is coated with gold.

\* \* \* \* \*